(12) United States Patent
Zabrecky

(10) Patent No.: US 9,011,938 B2
(45) Date of Patent: *Apr. 21, 2015

(54) METHODS AND FORMULATIONS FOR TREATING CHRONIC LIVER DISEASE

(76) Inventor: George Zabrecky, Ridgefield, CT (US)

( * ) Notice: Subject to any disclaimer, the term of this patent is extended or adjusted under 35 U.S.C. 154(b) by 37 days.

This patent is subject to a terminal disclaimer.

(21) Appl. No.: 13/466,681

(22) Filed: May 8, 2012

(65) Prior Publication Data

US 2012/0219581 A1    Aug. 30, 2012

Related U.S. Application Data

(62) Division of application No. 12/572,732, filed on Oct. 2, 2009, now Pat. No. 8,197,861.

(60) Provisional application No. 61/102,110, filed on Oct. 2, 2008.

(51) Int. Cl.
| | |
|---|---|
| A01N 65/00 | (2009.01) |
| A61K 36/537 | (2006.01) |
| A61K 31/198 | (2006.01) |
| A61K 31/352 | (2006.01) |
| A61K 31/357 | (2006.01) |
| A61K 36/074 | (2006.01) |
| A61K 36/185 | (2006.01) |
| A61K 36/79 | (2006.01) |
| A61K 36/80 | (2006.01) |

(52) U.S. Cl.
CPC .............. *A61K 36/537* (2013.01); *A61K 31/198* (2013.01); *A61K 31/352* (2013.01); *A61K 31/357* (2013.01); *A61K 36/074* (2013.01); *A61K 36/185* (2013.01); *A61K 36/79* (2013.01); *A61K 36/80* (2013.01)

(58) Field of Classification Search
CPC .................................................... A61K 36/00
USPC ........................................................ 424/725
See application file for complete search history.

(56) References Cited

U.S. PATENT DOCUMENTS

| | | | |
|---|---|---|---|
| 4,456,597 A | 6/1984 | Kojima et al. | |
| 4,469,685 A | 9/1984 | Kojima et al. | |
| 6,069,167 A | 5/2000 | Sokol | |
| 6,136,316 A * | 10/2000 | Mehrotra et al. ............. | 424/725 |
| 6,596,762 B2 | 7/2003 | Sokol | |
| 6,664,287 B2 * | 12/2003 | Avery et al. .................... | 514/436 |
| 6,884,908 B2 | 4/2005 | Srivastava et al. | |
| 7,078,064 B2 | 7/2006 | Zabrecky | |
| 7,381,435 B2 | 6/2008 | Yoshida et al. | |
| 7,682,617 B2 | 3/2010 | Olalde Rangel et al. | |
| 2003/0044512 A1 | 3/2003 | Watson et al. | |
| 2006/0063781 A1 | 3/2006 | Kim et al. | |
| 2006/0160898 A1 | 7/2006 | Bassaganya-Riera | |
| 2006/0275838 A1 | 12/2006 | Ray et al. | |
| 2007/0265340 A1 | 11/2007 | Shalwitz et al. | |
| 2007/0292507 A1 | 12/2007 | Smith | |
| 2008/0160042 A1 | 7/2008 | Olalde Rangel | |
| 2008/0233220 A1 * | 9/2008 | Zhong et al. ................... | 424/746 |
| 2010/0204093 A1 * | 8/2010 | Kaushal et al. ................ | 514/12 |

FOREIGN PATENT DOCUMENTS

| | | | |
|---|---|---|---|
| CN | 1879854 | * | 12/2006 |
| EP | 1 637 153 A1 | | 3/2006 |
| JP | 63027435 U | | 2/1988 |
| WO | WO 98/01144 A1 | | 1/1998 |
| WO | WO 2004/096252 A1 | | 11/2004 |
| WO | WO 2007/059441 A2 | | 5/2007 |
| WO | WO 2008/050344 A1 | | 5/2008 |

OTHER PUBLICATIONS

International Search Report and Written Opinion for Application No. PCT/US2009/059389 dated Feb. 15, 2010.
Abe, Y. et al., *Effectiveness of Interferon, Glycyrrhizin Combination Therapy in Patients with Chronic Hepatitis C*, Nippon Rinsho., 52(7), 1994, pp. 1817-1822.
Bacon, B.R. et al., *Nonalcoholic Steatohepatitis: An Expanded Clinical Entity*, Gastroenterology, vol. 107, No. 4, Oct. 1994, pp. 1103-1109.
Boigk, G. et al., *Silymarin Retards Collagen Accumulation in Early and Advanced Biliary Fibrosis Secondary to Complete Bile Duct Obliteration in Rats*, Hepatology, Sep. 1997, pp. 643-649.
Bustamante, J. et al., *Alpha-Lipoic Acid in Liver Metabolism and Disease*, Free Radical Biology & Medicine, vol. 24, No. 6, 1998, pp. 1023-1039.
Cheng, Y. et al., *Synergistic Effect of a Novel Oxymatrine-Baicalin Combination Against Hepatitis B Virus Replication, a Smooth Muscle Actin Expression and Type I Collagen Synthesis in vitro*, World J Gastroenterol, 12(32), Aug. 2006, 1 page.
Dharmananda, S. et al., *Oxymatrine Update on Clinical Effects and Safety*, available at mhtml:file://C:\Documents and Settings\George\Desktop\HarvardNA . . . , dated Sep. 23, 2009, 8 pages.
Gabbay, E. et al., *Anitoxidant Therapy for Chronic Hepatitis C after Failure of Interferon: Results of Phase II Randomized, Double-Blind Placebo Controlled Clinical Trial*, World Journal of Gastroenterology, vol. 13, No. 40, Oct. 2007, pp. 5317-5323.
Gong, G. et al., *Human Hepatitis C Virus NS5A Protein Alters Intracellular Calcium Levels, Induces Oxidative Stress, and Activates STAT-3 and NF-kappa B*, Proc. Nat'l. Acad. Sci. USA, vol. 98, No. 17, Aug. 2001, pp. 9599-9604.
Hargreaves, R. J. et al., *Studies on the Effects of L-Ascorbic Acid on Acetaminophen-Induced Hepatotoxicity II. An in vivo Assessment in Mice of the Protection Affored by Various Dosage Forms of Ascorbate*, Toxicology and Applied Pharmacology, 64, 1982, pp. 380-392.

(Continued)

Primary Examiner — Michael Meller
(74) Attorney, Agent, or Firm — Alston & Bird LLP

(57) ABSTRACT

An anti-inflammatory and anti-fibrotic antioxidant formulation for treatment of hepatic oxidative stress and cirrhosis is disclosed. The antioxidant formulation can further include at least one of a hepatitis C virus-specific or a non-alcoholic steatohepatitis-specific formulation comprising one or more compounds to retard the progression of liver fibrosis and possibly reverse an established fibrosis. Methods of treatment or therapies for treating chronic liver disease and chronic hepatitis are also provided.

10 Claims, 4 Drawing Sheets

(56) References Cited

OTHER PUBLICATIONS

Hill, D. B. et al., *Antioxidants Attenuate Nuclear Factor-Kappa B Activation and Tumor Necrosis Factor-Alpha Production in Alcoholic Hepatitis Patient Monocytes and Rat Kupffer Cells*, in vitro, Clinical Biochemistry, vol. 32, No. 7, Oct. 1999, pp. 563-570.

Hughes, C. A. et al., *Chronic Hepatitis C Virus Management: 2000-2005 Update*, The Annals of Pharmacotherapy, vol. 40, Jan. 2006, pp. 74-82.

Koike, K., *Molecular Basis of Hepatitis C Virus—Associated Hepatocarcinogenesis: Lessons from Animal Model Studies*, Clinical Gastroenterology and Hepatology, Oct. 2005, pp. S132-S135.

Li, Y. et al., *Anti-Hepatitis Activities in the Broth of Ganoderma lucidum Supplemented with a Chinese Herbal Medicine*, The American Journal of Chinese Medicine, vol. 34, No. 2, 2006, pp. 341-349.

Liu, K. T. et al., *Pharmacological Properties of Dibenzo [a, c] Cyclooctene Derivatives Isolated from Fructus Shisandra Chinensis III. Inhibitory Effects on Carbon Tetrachloride-Induced Lipid Peroxidation, Metabolism and Covalent Binding and Carbon Tetrachloride to Lipids*, Chem. Biol. Interactions, 41, 1982, pp. 39-47.

Liu, G. T. et al., *Protective Action of Seven Natural Phenolic Compounds Against Peroxidative Damage to Biomembranes*, Biochemicals Pharmacology, vol. 43, No. 2, Jan. 1992, pp. 147-152.

Liu, D. et al., *Protective Effect of Paeoniflorin on Immunological Liver Injury Induced by Bacillus Calmette-Guerin plus Lipopolysaccharide: Modulation of Tumour Necrosis Factor-α and Interleukin-6 mRNA*, Clinical and Experimental Pharmacology and Physiology, 33, 2006, pp. 332-339.

Loffelhardt, S. et al., *Interaction of Apha-Lipoic Acid Enantiomers and Homologues with the Enzyme Components of the Mammalian Pyruvate Dehydrogenase Complex*, Biochemical Pharmacology, vol. 50, No. 5, 1995, pp. 637-646.

Lu, H. et al., *Effect of Dibenzo [a, c]Cycloocten Lignans Isolated from Fructus Shisandra on ADPH Induced Lipid Peroxidation (Malondialdehyde MDA) Formation) and Anti-Oxidative Enzyme Activity*, Chem.-Biol. Interactions, 78, 1991, pp. 77-84.

Lu, L. G. et al., *Oxymatrine in the Treatment of Chronic Hepatitis B for One Year, a Multicenter Random Double-Blind Placebo-Controlled Trial*, available at mhtml:file://C:\Documents and Settings\George\Desktop\NASH-Supp . . . , dated Sep. 23, 2009, 2 pages.

Lu, L.G. et al., *Oxymatrine Therapy for Chronic Hepatitis B: A Randomized Double-Blind and Placcebo-Controlled Multi-Center Trial*, World J. Gastroenterol, 9(11), 2003, pp. 2480-2483.

Mao, Y. M. et al., *Capsule Oxymatrine in Treatment of Hepatic Fibrosis Due to Chronic Viral Hepatitis: A Randomized, Double Blind, Placebo-Controlled, Multicenter Clinical Study*, world J. Gasteroenterol, 10(22), 2004, pp. 3269-3273.

Oh, S. H. et al., *Salvia miltiorrhiza Inhibits Biliary Obstruction-Induced Hepatocyte Apoptosis by Cytoplasmic Sequestration*, Toxicol Appl. Pharmacol., vol. 182, Jul. 2002, pp. 27-33.

Pae, H. O. et al., *Inhibitory Effects of the Stem Bark of Catalpa ovata G. Don. (Bignoniaceae) on the Productions of Tumor Necrosis Factor-α and Nitric Oxide by the Lipopolisaccharide-Stimulated RAW 264.7 Macrophages*, Journal of Ethnopharmaclogy, vol. 88, 2003, 287-291.

Popov, Y. et al., *Halofuginone Induces Matrix Metalloproteinases in Rat Hepatic Stellate Cells via Activation of p38 and NFkappaB*, The Journal of Biological Chemical, vol. 281, No. 22, Jun. 2006, pp. 15090-15098.

Popov, Y. et al., *Pre-clinical evaluation of the antifibrotic efficacy of a formulation of defined naturally occurring antioxidants in the Mdr2-/-mouse model of biliary fibrosis*, AASLD, Abstract 1379, (2008), 2 pages.

Popov, Y. et al., *Mdr2 (Abcb4)-/- Mice Spontaneously Develop Sever Biliary Fibrosis vis Massive Dysregulation of Pro- and Antifibrogenic Genes*, Journal of Hepatology, 43, 2005, pp. 1045-1054.

Russo, A. et al., *Indian Medicinal Plants as Antiradicals and DNA Cleavage Protectors*, Phytomedicine, vol. 8, No. 2, 2001, pp. 125-132.

Schuppan, D. et al., *Liver Cirrhosis*, Seminar, Lancet, vol. 371, Mar. 2008, pp. 838-851.

Schuppan, D. et al., *Evaluation of the Anti-Inflammatory and Anti-Fibrotic Effect of Oral Antioxisant Formulations (Prep-X) in Experimental Models of Hepatic Oxidative Stress and Cirrhosis*, Final Report for The Billi and Bernie Marcus Foundation, Apr. 29, 2008, 18 pages.

Sun, F. et al., *Evaluation of Oxidative Stress Based on Lipid Hydroperoxide, Vitamin C and Vitamin E During Apoptosis and Necrosis Caused by Thioacetamide in Rat Liver*, Biochimica et Biophysica Acta 1500, 2000, pp. 181-185.

Takyar, S. S. et al., *Vitamin B12 Stalls the 80 S Ribosomal Complex on the Hepatitis C Internal Ribosome Entry Site*, J. Mol. Biol., 319, 2002, pp. 1-8.

Vaidya, A. B. et al., *Picrorhiza kurroa (Kutaki) Royle ex Benth as a Hepatoprotective Agent—Experimental and Clinical Studies*, J. Postgrad. Med., 42, 1996, pp. 105-108.

Valnezuela, A. et al., *Biochemical Bases of the Pharmacological Action of the Flavonoid Silymarin and of its Structural Isomer Silibini*, Biol. Res., vol. 27, No. 2, 1994, pp. 105-112.

Wang, J. et al., *Effect of Berberine Hydrochloride on Nonalcoholic Fatty Liver Disease in Rats*, Journal of Lanzhou University (Medical Sciences), vol. 33, No. 4, Dec. 2007, pp. 8-11.

Waris, G. et al., *Hepatitis C Virus Constitutively Activates STAT-3 via Oxidative Stress: Role of STAT-3 in HCV Replication*, Journal of Virology, vol. 79, No. 3, Feb. 2005, pp. 1569-1580.

Zabrecky, G., *Investigation of Hepaleve A Botanical Combination for Use in the Treatment of Hepatitis C and Non-Alcoholic Steatotic Hepatitis*, Investigator's Brochure, Jan. 2009, 6 pages.

Kutaki Picrorhiza kurroa Ayurvedic Liver Care Ayurveda Ayurvedic . . . , available at mhtml:file://C:\Documents and Settings\George\Desktop\NASH-Supp . . . , dated Sep. 23, 2009, 3 pages.

Picrorhiza, available at mhtml:file://C:\Documents and Settings\George⊃Desktop\NASH-Supp . . . , dated Sep. 23, 2009, 3 pages.

Picroliv® 5% Apocynin, Sabinsa Corporation, Finished Product Specification, 1 page.

Treatment of chronic hepatitis C virus infection . . . [J Clin Gastroenterol. 2005] PubMed . . . [online] [retrieved Jun. 16, 2008]. Retrieved from the Internet: <URL: http://www.ncbi/nlm.nih.gov/pubmed/16082287>. 2 pages.

Office Action from European Patent Application No. 09740785.2 dated Feb. 17, 2012.

Office Action from European Patent Application No. 09740785.2 dated Sep. 16, 2013.

Liu, G. et al.; "Protective Action of Seven Natural Phenolic Compounds Against Peroxidative Damage to Biomembranes"; *Biochemical Pharmacology*, 43(2):147-52 (1992).

Melhem, A. et al.; "Treatment of Chronic Hepatitis C Virus Infection Via Antioxidants: Results of a Phase I Clinical Trial"; *J. Clin Gastroenerol.* Sep. 2005; 39(8): 737-42.

\* cited by examiner

METHODS AND FORMULATIONS FOR TREATING CHRONIC LIVER DISEASE

CROSS REFERENCE TO RELATED APPLICATIONS

This application claims priority to U.S. Provisional Patent Application No. 61/102,110, filed on Oct. 2, 2008, which is incorporated by reference herein in its entirety. This application also claims priority to and is a divisional application of U.S. patent application Ser. No. 12/572,732 filed Oct. 2, 2009.

FIELD OF INVENTION

The present invention relates to formulations and methods for the treatment or prevention of chronic liver disease such as alcohol or toxic chemical induced cirrhosis or fibrosis, chronic hepatitis C virus infection, and/or non-alcoholic steatohepatitis. In particular, the invention relates to antioxidant formulations optionally supplemented with additional formulations directed to the treatment of specific causes of chronic liver disease such as a hepatitis C virus infection and non-alcoholic steatohepatitis. The invention also relates to methods of treating chronic liver disease, in particular, methods of treating chronic liver disease using the formulations of the invention.

BACKGROUND OF THE INVENTION

Chronic liver disease is marked by the gradual destruction of liver tissue over time. Several liver diseases fall under this category, including cirrhosis and fibrosis, the latter of which is often the precursor to cirrhosis.

Cirrhosis is the result of acute and chronic liver disease and is characterized by the replacement of liver tissue by fibrotic scar tissue and regenerative nodules leading to a progressive loss of liver function. Fibrosis and nodular regeneration results in the loss of the normal microscopic lobular architecture of the liver. Fibrosis represents the growth of scar tissue resulting from, for example, infection, inflammation, injury, and even healing. Over time, the fibrotic scar tissue slowly replaces the normal functioning liver tissue resulting in a decreasing amount of blood flow to the liver leaving the liver incapable of fully processing nutrients, hormones, drugs, and poisons that are found in the bloodstream. More common causes of cirrhosis include alcoholism, hepatitis C viral infections, ingestion of toxins, and fatty liver, but many other possible causes also exist.

Chronic hepatitis C virus (HCV) infection and non-alcoholic steatohepatitis (NASH) are the two major causes of chronic liver disease in the United States estimated to affect between 3-5 million people. A rising concern is the continuously increasing number of U.S. citizens, currently numbering over 30 million, with obesity and metabolic syndrome that have non-alcoholic fatty liver disease (NAFLD) with approximately 10% who will eventually develop NASH.

Other bodily complications are a consequence of a loss of liver function. The most common complication of cirrhosis is a condition known as ascites, an accumulation of fluid in the peritoneal cavity, which can lead to an increased risk of spontaneous bacterial peritonitis possibly resulting in the premature death of the patient.

Other potentially life-threatening complications of cirrhosis include hepatic encephalopathy, a neuropsychotic abnormality resulting when toxic substances that normally are removed by the liver from blood begin to impair the proper functioning of brain cells. Hepatic encephalopathy manifests itself in a widely varying array of quantitative and qualitative distinct features, depending on the severity of impairment that occurs. The resulting cerebral dysfunction can be mild, manifesting itself through neuropsychiatric and psychomotor dysfunction, impaired memory, increased reaction time, sensory abnormalities and poor concentration. More severe manifestations resulting from hepatic encephalopathy include confusion, stupor, coma, and even eventual death. There are at least four theories for the pathogenesis of the condition. One theory suggests an energy failure in the cerebrum resulting from impaired glucose oxidative pathways caused by liver failure that leads to increased lactate synthesis in the brain. Another theory supports the notion of energy failure in the cerebrum but resulting instead from hypoglycemia and hypoxia caused by impaired liver function. A third theory suggests that the liver's failure to convert ammonia to urea or glutamine causes an increased concentration of the component in the bloodstream resulting in hyperammonemia in the brain eventually leading to the death of brain cells. A final theory for pathogenesis of hepatic encephalopathy is that any decrease in glucose utilization to provide energy to the brain is compensated for by the mobilization of amino acids that provide carbon skeletons as substrates for energy metabolism; however, the proteolysis of cerebral proteins to compensate for any energy loss ultimately proves destructive to proper functioning of the brain.

Yet another potentially life-threatening complication of cirrhosis includes esophageal varices or extremely dilated sub-mucosal veins in the esophagus that are susceptible to bleeding.

Once any cirrhosis or fibrosis has occurred in the liver, it is generally considered irreversible. Rather, conventional treatment focuses on preventing any further progression of cirrhosis in the liver and mitigating the complications that can arise from cirrhosis. In more advanced stages of cirrhosis, the only conventionally known treatment is a liver transplant.

The American Liver Foundation estimates that over 300,000 people in the United States are hospitalized each year as a result of cirrhosis of the liver. It is also estimated that 18,000 people are in need of liver transplants.

There remains a need in the art for a composition, formulation, and/or method of treatment for inhibiting fibrosis, preventing the development of cirrhosis, and possibly reversing development of the conditions altogether, which are responsible for many of the life-threatening complications associated with chronic hepatitis and chronic liver disease, such as, for example, excessive bleeding from esophageal varices, mental disturbances due to hepatic encephalopathy, ascites, liver cancer, and death due to exhaustion of liver function.

There remains a need in the art for a composition, formulation, therapy, and/or effective treatment to inhibit the progression of fibrosis in patients suffering from acute or chronic liver disease. There remains a further need in the art for a composition, formulation, therapy, or effective treatment to induce fibrosis reversal in patients suffering from acute or chronic liver disease. There remains a further need in the art for a composition, formulation, therapy or effective treatment to inhibit the progression of fibrosis and/or induce fibrosis reversal in patients suffering from acute or chronic liver disease that is substantially free of side effects.

HCV is a member of the *hepacivirus* genus of the Flaviviradae family of viruses. HCV can be classified into six genetic groups otherwise known as HCV clades that can further be classified into over 100 subtypes. The clades and subtypes differ from each other at the nucleotide level. Chronic hepatitis, experienced by well over 75% of persons infected, ultimately leads to cirrhosis of the liver in approximately 20% of those persons chronically infected and liver cancer leading to deaths of between 1% and 5% of those persons chronically infected. It is estimated that 3.5 million people have chronic hepatitis in the United States.

The pathogenesis of chronic HCV infection is associated with both a defective host antiviral immune response and an intrahepatic oxidative stress. Oxidative stress is possibly induced by the combined effects of an inflammatory response by the host and the HCV non-structural viral proteins. Additionally, oxidative stress and lipid oxidation are known to play a major role in fatty liver accumulation, which leads to necro-inflammation and necrosis of hepatic cells.

HCV non-structural viral proteins have been shown to cause activation of STAT-3 through oxidative stress and Ca2+ signaling. See Gong et al., "Human Hepatitis C Virus NS5A Protein Alters Intracellular Calcium Levels, Induces Oxidative Stress, and Activates STAT-3 and NF-kappa B," *Proc. Nat'l. Acad. Sci. USA*, 98:9599-604 (2001). STAT-3 induction is influenced by the activation of cellular kinases, including p38 mitogen-activated protein kinase, JNK, JAK-2, and Src. In vivo experiments showed STAT-3 induction becomes inhibited in the presence of an antioxidant. It has been reported that HCV core protein increases radical oxygen species as well as products of lipid peroxidation and antioxidant gene expression. See Waris et al., "Hepatitis C Virus Constitutively Activates STAT-3 via Oxidative Stress: Role of STAT-3 in HCV Replication," *J. Virol.*, 79:1569-80 (2005). These processes are thought to contribute to fibrosis and carcinogenesis in hosts with chronic HCV infections. See Koike, "Molecular Basis of Hepatitis C Virus-Associated Hepatocarcinogenesis: Lessons from Animal Model Studies," *Clin. Gastroenterol Hepatol*, 3:Sβ2-S135 (2005).

Fatty liver, also known as steatosis, is a disease that is characterized by an excessive amount of lipids accumulating in the liver. Fatty liver may develop due to medicine or alcohol use, viral or bacterial infections, or obesity. Fatty liver and conditions stemming from fatty liver include NASH, liver inflammation, cirrhosis, and liver failure. Steatohepatitis is inflammation of the liver resulting from fat accumulation in the liver.

NASH, also known as non-alcoholic fatty liver disease, is a hepatic disorder that is typically characterized by an alcoholic pathogenesis but without being influenced by alcohol consumption. Rather, NASH is directly related to the amount of fat in the liver. While there are many possible causes of NASH, the most likely causes that have been identified include obesity due to a poor diet, diabetes, long-term use of steroids, and the use of tetracycline. See, e.g., Bacon et al., "Nonalcoholic Steatohepatitis: An Expanded Clinical Entity," *Gastroenterology*, 107:1103-91 (1994).

Recent studies have shown that oxidative stress and lipid peroxidation play a major role in fat accumulation in the liver, or steatosis, that leads to necroinflammation and necrosis of hepatic cells. Steatosis, and the ensuing lipid peroxidation, can lead to activation of stellate cells, the cells in the liver that are principally responsible for fibrogenesis. Some research has been directed towards identifying compositions comprising antioxidants that would be useful to treat the oxidative stress and/or lipid peroxidation associated with NASH.

Antioxidative therapy, directed towards mitigating the intrahepatic oxidative stress pathway, has been shown to have a beneficial effect on patients with chronic HCV infection. For example, U.S. Pat. No. 7,078,064 to Zabrecky discloses compositions having antioxidants that are useful for treating chronic liver disease, chronic hepatitis C virus infection, and non-alcoholic steatohepatitis. U.S. Pat. No. 6,069,167 to Sokol discloses the use of certain antioxidant agents including vitamin E, carotenoids, and selenium to treat cholestatic liver disease. U.S. Pat. No. 6,596,762 to Sokol discloses an antioxidant composition consisting of soluble vitamin E, mixed carotenoids, and selenium for the treatment of hepatic steatosis. These references report in vivo testing showing a high dosage of antioxidant administered to the subject relative to the subject's body weight. These references further show the administration therapies must be frequent and continue long-term.

The safety and efficacy of antioxidant therapy for patients with chronic HCV infection, in particular, for those patients who failed in interferon treatment has been reported in Gabby et al., "Antioxidant Therapy for Chronic Hepatitis C after Failure of Interferon: Results of Phase II Randomized, Double-Blind Placebo Controlled Clinical Trial," *World J. Gastroenterol.*, 13(4):5317-23 (2007). 100 patients suffering chronic HCV infection were enrolled in this double-blind, placebo controlled single-center trial. The study involved two treatment options involving 50 patients in each section. The first part tested the administration of oral and intravenous antioxidant preparations versus that of a placebo. The second part tested the administration of only the oral preparations versus a placebo. 25 patients were randomly assigned to each of the treatment group and the placebo group.

The oral and intravenous combinations are shown below:

| | Patient Dose | |
|---|---|---|
| Component | Oral Combination | Intravenous Combination |
| Glycyrrhiza | 500 mg bid | 120 mg |
| Schizandrae | 500 mg tid | — |
| Ascorbate | 2,000 mg tid | 10,000 mg |
| L-Glutathione | 150 mg tid | 750 mg |
| Silymarin | 250 mg tid | — |
| Lipoic Acid | 150 mg bid | — |
| d-Alpha Tocopherol | 800 IU/d | — |
| B-comple | — | 1 mL |

Patients in the treatment groups of both studies received the oral combination once daily for 24 weeks. Patients in the treatment group of the first study additionally received the intravenous combination by injection with 400 mL of normal saline for infusion twice a week for the first ten weeks of the study. Patients in the placebo groups received pills resembling those of the treatment group and the normal saline intravenously.

The results of the study for each of the treatment group and the placebo group over the course of the study are given below.

| | Oral and Intravenous Antioxidant Formulations | | | | | | Oral Antioxidant Formulation Only | | | | | |
|---|---|---|---|---|---|---|---|---|---|---|---|---|
| | ALT IU | | AST IU | | HCV RNA Serum log(copies/ml) | | ALT IU | | AST IU | | HCV RNA Serum log(copies/ml) | |
| Week | Treated | Placebo | Treated | Placebo | Treated | Placebo | Treated | Placebo | Treated | Placebo | Treated | Placebo |
| 0 | 75.0 | 70.2 | 79.3 | 75.6 | 5.36 | 5.16 | 86.4 | 76.7 | 70.2 | 74.2 | 4.84 | 5.16 |
| 10 | 64.7 | 67.3 | 70.0 | 69.5 | — | — | — | — | — | — | — | — |

-continued

| | Oral and Intravenous Antioxidant Formulations | | | | | | Oral Antioxidant Formulation Only | | | | | |
|---|---|---|---|---|---|---|---|---|---|---|---|---|
| | ALT IU | | AST IU | | HCV RNA Serum log(copies/ml) | | ALT IU | | AST IU | | HCV RNA Serum log(copies/ml) | |
| Week | Treated | Placebo | Treated | Placebo | Treated | Placebo | Treated | Placebo | Treated | Placebo | Treated | Placebo |
| 12 | — | — | — | — | 5.20 | 5.28 | 66.6 | 74.7 | 72.5 | 78.6 | 4.97 | 5.20 |
| 24 | 64.8 | 75.0 | 61.7 | 78.5 | 5.08 | 5.04 | 63.5 | 81.8 | 65.7 | 81.8 | 5.36 | 5.28 |
| 32 | 62.7 | 68.2 | 58.6 | 66.9 | 5.30 | 5.10 | 74.1 | 57.6 | 69.7 | 74.5 | 5.35 | 5.28 |
| 40 | 66.6 | 62.1 | 66.9 | 67.5 | 5.35 | 5.31 | 71.8 | 96.5 | 65.5 | 78.5 | 5.33 | 5.72 |
| 48 | 63.0 | 58.3 | 73.1 | 69.3 | 5.71 | 5.35 | 83.9 | 61.8 | 92.7 | 69.5 | 4.94 | 5.25 |

The data shows that the combined use of oral and intravenous antioxidant formulations only mildly alleviate the intra-hepatic inflammatory response in patients suffering a chronic HCV infection while no effect is shown by using only the oral antioxidant treatment.

There remains a need in the art for an antioxidant formulation that can be administered as part of a treatment therapy to effectively prevent, retard, and/or reverse the effects of a chronic liver disease. There remains a further need in the art for an antioxidant composition that can be administered as part of a treatment therapy for acute or chronic liver disease that is substantially free of side effects. There remains a further need in the art for an antioxidant composition that can be administered as part of a treatment therapy for acute or chronic liver disease that is affordable.

Conventionally, the treatment of chronic HCV is a combination therapy including pegylated interferons and ribavirin. However, the response rate of the treatment's pharmacological efficacy and adverse effects is approximately 55% in patients infected with the genotype I virus. See Hughes et al., "Chronic Hepatitis C Virus Management: 2000-2005 Update," *Ann. Pharmacother,* 40:74-82 (2006).

There remains a need in the art for a therapy to treat chronic HCV infected patients, especially for those patients who are non-responsive to conventional treatment therapies.

The use of alternative medicine is common in patients with chronic liver disease. For example, compositions comprising antiviral active components derived from herbal medicinal plants have traditionally been used in China for the treatment of hepatitis B virus, HCV, and HIV. Indeed, many modern drugs contain ingredients that are derived from herbs. The more conventionally termed alternative medicine, traditionally known as "folk" medicine, involves the use of herbal medicines in the care and treatment of the sick. Alternative medicine strategies have become more accepted in the western scientific medical community particularly as the development of pharmaceutical compounds have failed to keep pace with the ever-growing knowledge of pathogenesis pathways of various viral infections and diseases.

In fact, it has come to be known that many traditional herbal formulations lead to an in vivo response that can produce the pharmacological ingredient leading to the desired host response to combat the infection or disease. For example, the Chinese herbal medicine Aeginetiae Herba has traditionally been used to treat, among other things, liver disease. Aeginaetiae Herba is prepared from the dried whole plant of *Aeginetia indica*. A phosphate buffered saline extract from the seeds of *Aeginetia indica* has been shown to exhibit excellent carcinostatic effect possessing interleukin 2 and interferon y inducing potency effect. The Chinese herbal medicine Scutellariae Barbatae Herba derived from dried whole plants of *Scutellaria rivularis* have traditionally been used for the treatment of hepatitis and liver cirrhosis. The traditional Chinese practice of prescribing herbal medicines was in response to symptoms of a patient typically after a disease or agent itself had progressed to more advanced stages of development in the patient.

A method of producing an interferon inducer from the plants of the genus Cucurbitaceae, such as from a pumpkin seed, is disclosed in U.S. Pat. No. 4,421,746 to Kojima et al. U.S. Pat. No. 4,456,597 to Kojima et al. discloses an antiviral and anti-tumor activity of interferon inducers that are extracted from the flowers of *Carthamus tinctorious*. U.S. Pat. No. 4,469,685 also to Kojima et al. discloses that interferon inducers useful for the treatment of viral infections in humans may be extracted from the flowers of *Lonicera japonica* and the seeds of *Plantago asiatica*.

Traditional Chinese and Ayurvedic therapies or treatment strategies have focused on the use of herbal formulations having many components, but it is not entirely clear whether a single component within the formulation or the combination of a collection of components within the formulation are responsible for the medicinal or therapeutic benefit. However, it is duly noted, that such a concept does run counter to the traditional western medicine concept of pharmacological treatment, which is focused on the delivery of a single compound or drug for the treatment of an infection, condition, disease, and the like.

There remains a need in the art to explore and identify alternative medicine treatments, either used alone or in a complimentary treatment strategy, generally for patients suffering from cirrhosis of the liver and, specifically, for patients having a chronic liver disease.

BRIEF SUMMARY OF THE INVENTION

The present invention relates to methods and compositions comprising at least one antioxidant and, optionally, supplemental actives to slow the progression of, reverse or resolve, treat or prevent chronic liver disease. Without intending to be bound by theory, the formulations of the invention, and the methods of treatment provide an improved capability to retard a fibrosis and/or cirrhosis, either occurring or that would otherwise occur, in the liver and possibly reverse the progression of a fibrosis and/or cirrhosis occurring in the liver. In specific embodiments of the invention, the formulations of the invention provide an improved capability to retard a fibrosis and/or cirrhosis, either occurring or that would otherwise occur, in the liver and possibly reverse the progression of a fibrosis and/or cirrhosis occurring in the liver resulting from a chronic hepacivirus C virus (HCV) infection or a non-alcoholic steatohepatitis (NASH). When used in a treatment regimen, the inventive formulations include constituents that work synergistically to satisfy many of the needs in the art.

In one aspect, the invention provides a formulation for the treatment of a chronic liver disease comprising an antioxidant component and one of an HCV active constituent and a NASH active constituent. In an embodiment of the invention, the antioxidant component is selected from *Salvia miltiorrhiza; Schisandra chinensis*; oleanolic acid or a pharmaceutically acceptable salt thereof; *Ganoderma lucidum*; silymarin; α-lipoic acid, more preferably R isomer α-lipoic acid; N-acetyl cysteine; *Picrorhiza kurroa*; any extract of the plant or herbal components; and any combination thereof. The HCV active constituent is selected from the group consisting of *Picrorhiza kurroa*, any extract of *Picrorhiza kurroa*, baicalin/baicalein, and any combination thereof. The NASH active constituent is selected from the group consisting of baicalin/baicalein, paeoniflorin, berberine, *Catalpa ovata, Picrorhiza kurroa*, any extract of the plant or herbal constituents, and any combination thereof.

In certain embodiments of the invention, the chronic liver disease is caused by a chronic HCV infection. In certain preferred embodiments of the invention, the antioxidant component of the formulation comprises *Salvia miltiorrhiza* or any extract thereof, *Schisandra chinensis* or any extract thereof, oleanolic acid or a pharmaceutically acceptable salt thereof, *Ganoderma lucidum* or any extract thereof, silymarin, α-lipoic acid, N-acetyl cysteine, and *Picrorhiza kurroa* or any extract thereof, and the HCV active constituent of the formulation comprises baicalin/baicalein.

In certain embodiments of the invention, the chronic liver disease is caused by NASH. In certain preferred embodiments of the invention, the antioxidant component of the formulation comprises *Salvia miltiorrhiza* or extract thereof, *Schisandra chinensis* or extract thereof, oleanolic acid or a pharmaceutically acceptable salt thereof, *Ganoderma lucidum* or extract thereof, silymarin, α-lipoic acid, N-acetyl cysteine, and *Picrorhiza kurroa* or any extract thereof, and the NASH active constituent of the formulation comprises baicalin/baicalein, paeoniflorin, berberine, and *Catalpa ovata* or any extract thereof.

In certain embodiments of the invention, the formulation may be administered orally, parenterally, transdermally, epidurally, intranasally, and any combination thereof.

In an embodiment of the invention, the antioxidant component and any one of the HCV active constituent and the NASH active constituent are administered, either separately or together, orally by at least one of directly administering the formulations to a subject, optionally using at least one of a pharmaceutically acceptable carrier and a pharmaceutically acceptable excipient; incorporating the formulations into food to be consumed by the subject; and including the formulations in dietary supplements to be taken by the subject.

In an embodiment of the invention, any one of the HCV active constituent and the NASH active constituent is administered at least one of prior to, for a therapeutically effective amount of time; substantially contemporaneously with; and following, for a therapeutically effective amount of time, administration of the antioxidant component.

Another aspect of the invention provides methods for treating chronic liver disease, in particular, methods of treating chronic liver disease using the formulations of the invention. In an embodiment of the invention, the method for treating chronic liver disease comprises the step of administering at least one antioxidant formulation comprising an antioxidant selected from the group consisting of *Salvia miltiorrhiza; Schisandra chinensis*; oleanolic acid or a pharmaceutically acceptable salt thereof; *Ganoderma lucidum*; silymarin; α-lipoic acid, more preferably R isomer α-lipoic acid; N-acetyl cysteine; *Picrorhiza kurroa*; any extract of the plant or herbal components; and any combination thereof.

In a preferred embodiment of the invention, the method of treatment comprises administering at least two antioxidant formulations of the invention, one administered orally and the other administered by infusion or injection. According to another preferred embodiment of the invention, one of the two antioxidant formulations is administered daily and the other antioxidant formulation is administered biweekly.

In yet another embodiment of the invention, the method of treatment is a therapy to treat a chronic liver disease caused by a chronic HCV infection. This method of treatment further comprises the step of administering at least one HCV supplemental formulation. In an embodiment of the invention, the step of administering at least one HCV supplemental formulation includes administering an HCV supplemental formulation comprising an HCV active constituent. In an embodiment of the invention, the step of administering at least one HCV supplemental formulation preferably includes administering an HCV supplemental formulation comprising an HCV active selected from *Picrorhiza kurroa*, any extract of *Picrorhiza kurroa*, baicalin/baicalein, and any combination thereof.

In yet another embodiment of the invention, the method of treatment is a therapy to treat a chronic liver disease caused by NASH. This method of treatment further comprises the step of administering at least one NASH supplemental formulation. In an embodiment of the invention, the step of administering at least one NASH supplemental formulation includes administering an NASH supplemental formulation comprising an NASH active constituent. In an embodiment of the invention, the step of administering at least one NASH supplemental formulation preferably includes administering a NASH supplemental formulation comprising a NASH active selected from baicalin/baicalein, paeoniflorin, berberine, *Catalpa ovata, Picrorhiza kurroa*, any extract of the plant or herbal actives, and any combination thereof.

In another preferred embodiment of the invention, in particular when the chronic liver disease is caused by an HCV infection, the antioxidant component of the at least one antioxidant formulation comprises *Salvia miltiorrhiza* or any extract thereof, *Schisandra chinensis* or any extract thereof, oleanolic acid or a pharmaceutically acceptable salt thereof, *Ganoderma lucidum* or any extract thereof, silymarin, α-lipoic acid, N-acetyl cysteine, and *Picrorhiza kurroa* or any extract thereof, and the HCV active constituent of the at least one HCV supplemental formulation comprises baicalin/baicalein.

In yet another preferred embodiment of the invention, in particular when the chronic liver disease is caused by NASH, the antioxidant component of the at least one antioxidant formulation comprises *Salvia miltiorrhiza* or extract thereof, *Schisandra chinensis* or extract thereof, oleanolic acid or a pharmaceutically acceptable salt thereof, *Ganoderma lucidum* or extract thereof silymarin, α-lipoic acid, N-acetyl cysteine, and *Picrorhiza kurroa* or extract thereof, and the NASH active constituent of the at least one NASH supplemental formulation comprises baicalin/baicalein, paeoniflorin, berberine, and *Catalpa ovata* or any extract thereof.

In an embodiment of the invention, the method of treating a chronic liver disease involves administering any of the at least one HCV supplemental formulation or any of the at least one NASH supplemental formulation at least one of prior to, for a therapeutically effective amount of time; substantially contemporaneously with; and following, for a therapeutically effective amount of time, administration of any of the at least one antioxidant formulation.

Another aspect of the invention provides a kit for treating chronic liver disease comprising at least one antioxidant formulation having an antioxidant component selected from the group consisting of *Salvia miltiorrhiza; Schisandra chinensis*; oleanolic acid or a pharmaceutically acceptable salt thereof; *Ganoderma lucidum*; silymarin; α-lipoic acid, preferably R isomer α-lipoic acid; N-acetyl cysteine; *Picrorhiza kurroa*; any extract of the plant or herbal components; and any combination thereof.

In a preferred embodiment of the invention, the kit further comprises at least one supplemental formulation selected from the group consisting of an HCV supplemental formulation for treating a chronic liver disease caused by a chronic HCV infection and a NASH supplemental formulation for treating a chronic liver disease caused by NASH.

In an embodiment of the invention, the at least one antioxidant formulation and the at least one supplemental formulation may each individually or even collectively be provided in the form of a pharmaceutically acceptable carrier and a pharmaceutically acceptable excipient; a food to be consumed by a subject; a dietary supplement to be taken by the subject; and any combination thereof.

In an embodiment of the invention, the kit includes an HCV supplemental formulation comprising an HCV active constituent selected from the group consisting of *Picrorhiza kurroa*, any extract of *Picrorhiza kurroa*, baicalin/baicalein, and any combination thereof.

In another embodiment of the invention, the kit includes a NASH supplemental formulation comprising a NASH active constituent selected from the group consisting of baicalin/baicalein, paeoniflorin, berberine, *Catalpa ovata, Picrorhiza kurroa*, any extract of the plant or herbal constituents, and any combination thereof.

In a preferred embodiment of the invention, the kit is provided for the purpose of treating a chronic liver infection caused by an HCV infection and the antioxidant component of the at least one antioxidant formulation comprises *Salvia miltiorrhiza* or extract thereof, *Schisandra chinensis* or extract thereof, oleanolic acid or a pharmaceutically acceptable salt thereof, *Ganoderma lucidum* or extract thereof, silymarin, α-lipoic acid, N-acetyl cysteine, and *Picrorhiza kurroa* or extract thereof, and the HCV active constituent of the at least one HCV supplemental formulation comprises baicalin/baicalein.

In another preferred embodiment of the invention, the kit is provided for the purpose of treating a chronic liver infection caused by NASH and the antioxidant component of the at least one antioxidant formulation comprises *Salvia miltiorrhiza* or extract thereof, *Schisandra chinensis* or extract thereof, oleanolic acid or a pharmaceutically acceptable salt thereof, *Ganoderma lucidum* or extract thereof, silymarin, α-lipoic acid, N-acetyl cysteine, and *Picrorhiza kurroa* or any extract thereof, and the NASH active constituent of the at least one NASH supplemental formulation comprises baicalin/baicalein, paeoniflorin, berberine, and *Catalpa ovata* or any extract thereof.

In an embodiment of the invention, the kit additionally comprises instructions advising that the at least one antioxidant formulation and the at least one supplemental formulation should be administered any of orally, parenterally, transdermally, epidurally, and intranasally.

In an embodiment of the invention, the kit additionally comprises instructions advising any of the at least one supplemental formulation be administered at least one of prior to, for a therapeutically effective amount of time; substantially contemporaneously with; and following, for a therapeutically effective amount of time, administration of any of the antioxidant formulation.

Embodiments of the present invention thus provide significant advantages as otherwise detailed herein.

BRIEF DESCRIPTION OF THE SEVERAL VIEWS OF THE DRAWINGS

Figure 1A:
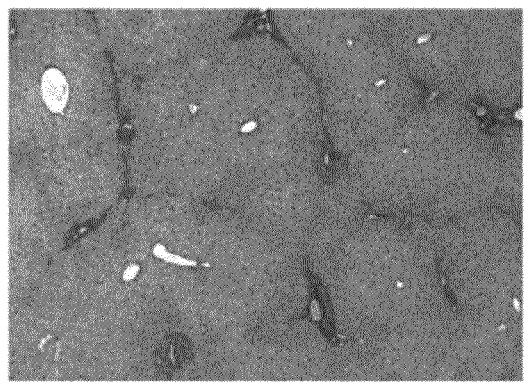
Figure 1B:
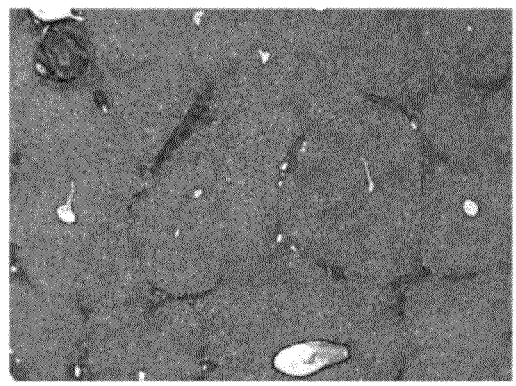
Figure 1C:
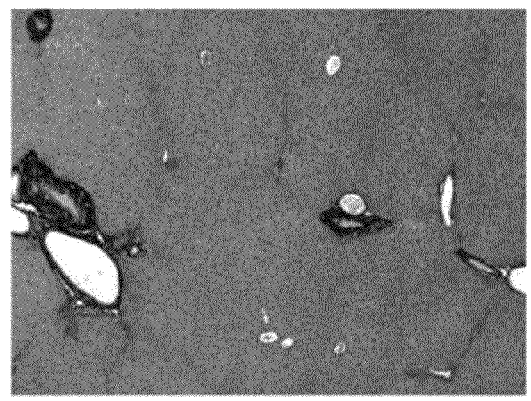
Figure 2A:
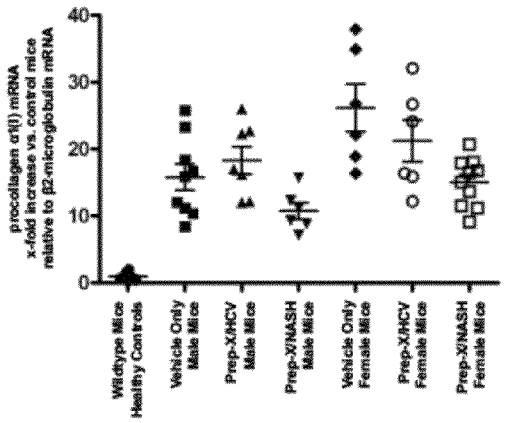
Figure 2B:
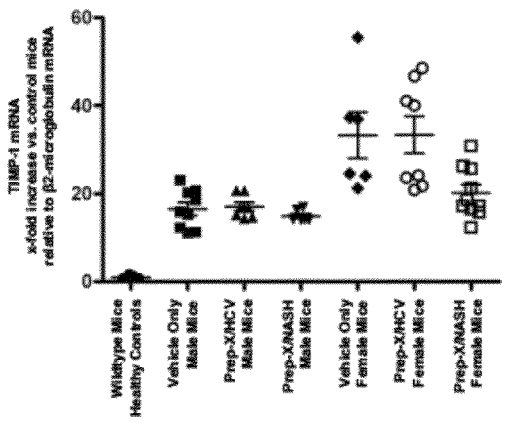
Figure 2C:
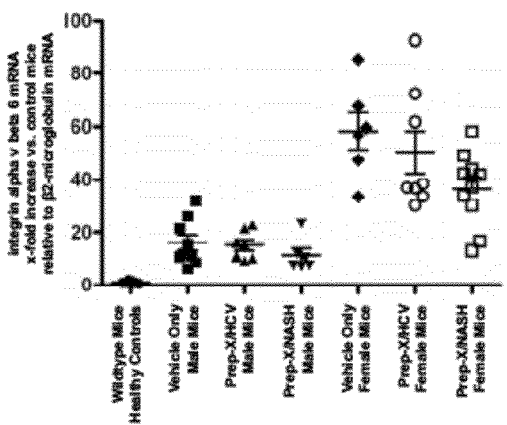
Figure 2D:
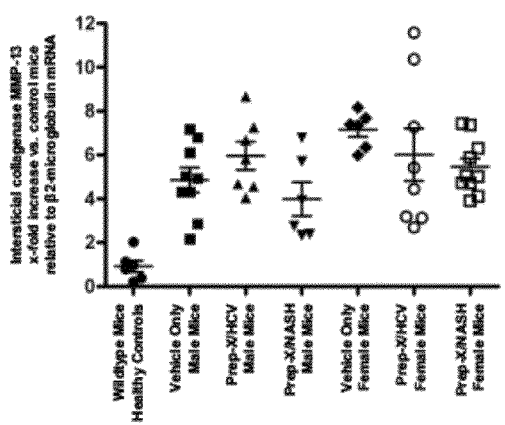
Figure 3A:
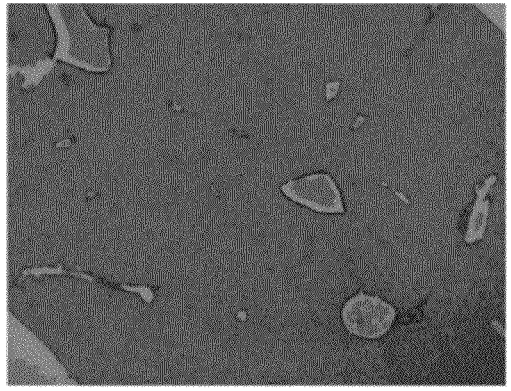
Figure 3B:
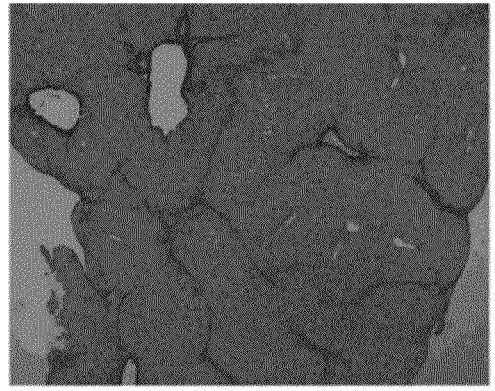
Figure 3C:
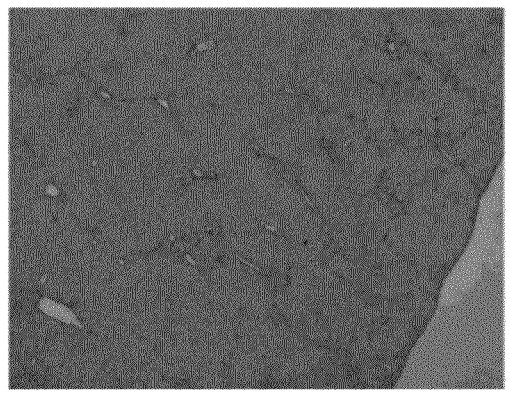
Figure 3D:
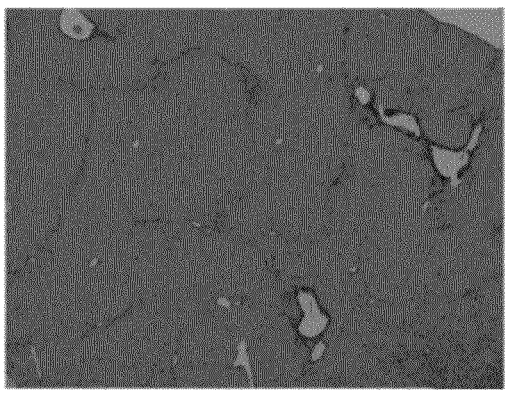
Figure 3E:
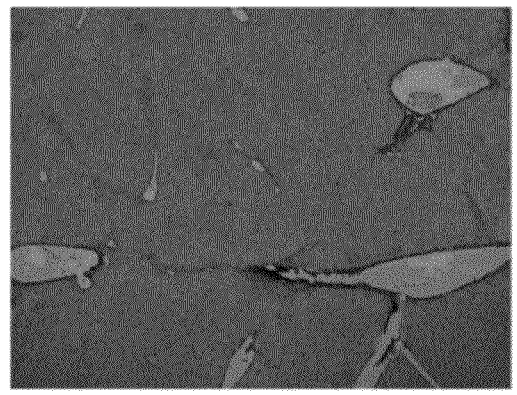
Figure 4A:
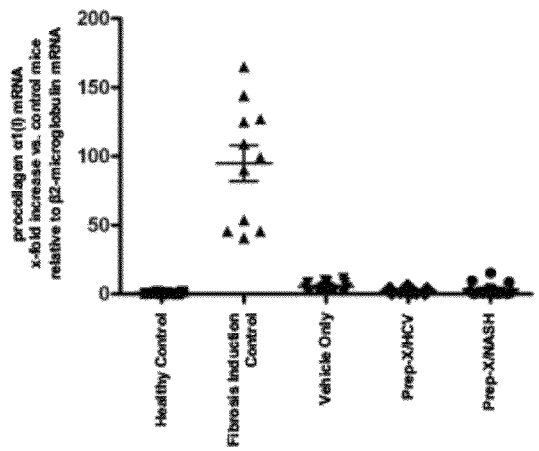
Figure 4B:
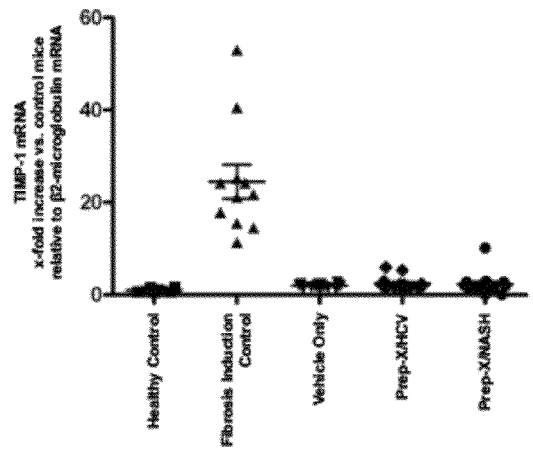
Figure 4C:
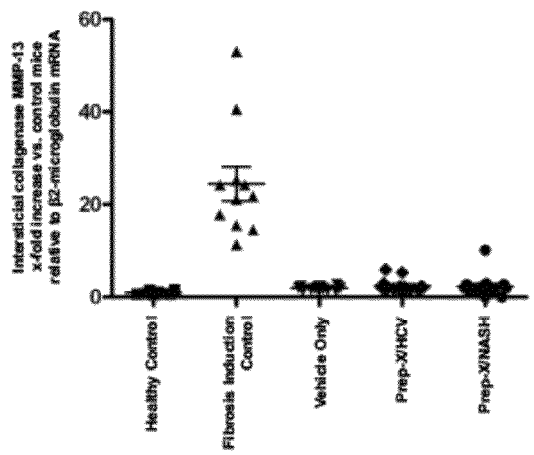

Having thus described the invention in general terms, reference will now be made to the accompanying drawings, which are not necessarily drawn to scale, and wherein:

FIG. 1A is an image of a representative liver section of a male mouse using connective tissue staining after undergoing treatment receiving only the vehicle over a six week period;

FIG. 1B is an image of a representative liver section of a male mouse using connective tissue staining after undergoing treatment receiving Prep-X over a six week period with the HCV-specific supplemental formulation included at the midway point of the combination treatment;

FIG. 1C is an image of a representative liver section of a male mouse using connective tissue staining after undergoing treatment receiving Prep-X over a six week period with the NASH-specific supplemental formulation included at the midway point of the combination treatment;

FIG. 2A represents profibrogenic gene expression of pro-collagen α1(1) encoding the major scar collagen expressed as x-fold increase versus the livers from the wildtype control mice in arbitrary units relative to the internal standard β2-microglobulin mRNA;

FIG. 2B represents profibrogenic gene expression of tissue inhibitor of matrix metalloproteinase-1 expressed as x-fold increase versus the livers from the wildtype control mice in arbitrary units relative to the internal standard β2-microglobulin mRNA;

FIG. 2C represents profibrogenic gene expression of profibrogenic, proliferating cholangiocyte-associated integrin alpha v beta 6 expressed as x-fold increase versus the livers from the wildtype control mice in arbitrary units relative to the internal standard β2-microglobulin mRNA;

FIG. 2D represents profibrogenic gene expression of interstitial collagenase matrix metalloproteinase-13 ("MMP-13") expressed as x-fold increase versus the livers from the wildtype control mice in arbitrary units relative to the internal standard β2-microglobulin mRNA;

FIG. 3A is an image of a representative liver section of a healthy C57BL/6J mouse using connective tissue staining;

FIG. 3B is an image of a representative liver section of a mouse using connective tissue staining after TAA-induction for six weeks;

FIG. 3C is an image of a representative liver section of a mouse using connective tissue staining after TAA-induction for six weeks and then undergoing treatment receiving only the vehicle over a four week period;

FIG. 3D is an image of a representative liver section of a mouse using connective tissue staining after TAA-induction for six weeks and then undergoing treatment receiving Prep-X over a four week period with the HCV-specific supplemental formulation included at the midway point of the combination treatment;

FIG. 3E is an image of a representative liver section of a mouse using connective tissue staining after TAA-induction for six weeks and then undergoing treatment receiving Prep-X over a four week period with the NASH-specific supplemental formulation included at the midway point of the combination treatment;

FIG. 4A represents profibrogenic gene expression of procollagen α1(1) encoding the major scar collagen expressed as x-fold increase versus the livers from the control mice in arbitrary units relative to the internal standard β2-microglobulin mRNA;

FIG. 4B represents profibrogenic gene expression of tissue inhibitor of matrix metalloproteinase-1 expressed as x-fold increase versus the livers from the control mice in arbitrary units relative to the internal standard β2-microglobulin mRNA; and FIG. 4C represents profibrogenic gene expression of interstitial collagenase matrix metalloproteinase-13 ("MMP-13") expressed as x-fold increase versus the livers from the control mice in arbitrary units relative to the internal standard β2-microglobulin mRNA.

DETAILED DESCRIPTION OF THE INVENTION

The present invention now will be described more fully hereinafter with reference to the accompanying figures. Preferred embodiments of the invention may be described, but this invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments of the invention are not to be interpreted in any way as limiting the invention.

As used in the specification and in the appended claims, the singular forms "a", "an", and "the" include plural referents unless the context clearly indicates otherwise. For example, reference to "a formulation" includes a plurality of such formulations.

Although specific terms are employed herein, they are used in a generic and descriptive sense only and not for purposes of limitation. All terms, including technical and scientific terms, as used herein, have the same meaning as commonly understood by one of ordinary skill in the art to which this invention belongs unless a term has been otherwise defined. It will be further understood that terms, such as those defined in commonly used dictionaries, should be interpreted as having a meaning as commonly understood by a person having ordinary skill in the art to which this invention belongs. It will be further understood that terms, such as those defined in commonly used dictionaries, should be interpreted as having a meaning that is consistent with their meaning in the context of the relevant art and the present disclosure. Such commonly used terms will not be interpreted in an idealized or overly formal sense unless the disclosure herein expressly so defines otherwise.

An aspect of the invention described herein relates to a treatment regimen comprising an antioxidant formulation, specifically, an antioxidant formulation used in the treatment of chronic liver disease. The antioxidant formulation is generally comprised of one or more or even all of the antioxidants or antioxidant components, as used interchangeably herein, Salvia miltiorrhiza; oleanoate or oleanolic acid; Ganoderma lucidum; silymarin; lipoic acid or α-lipoic acid, preferably R isomer α-lipoic acid; N-acetyl cysteine; glycyrrhiza; Schisandra chinensis; ascorbate or ascorbic acid; glutathione; vitamin E or any one of the vitamin E compounds such as α-tocopherol; vitamin B-complex or any one of the B vitamins; Picrorhiza kurroa; and oxymatrine. In a preferred embodiment of the invention, an antioxidant component of the antioxidant formulation is selected from Salvia miltiorrhiza; Schisandra chinensis; oleanolic acid or a pharmaceutically acceptable salt thereof; Ganoderma lucidum; silymarin; α-lipoic acid, more preferably R isomer of α-lipoic acid; N-acetyl cysteine; and any combination thereof. In another preferred embodiment of the invention, an antioxidant component of the antioxidant formulation is selected from Salvia miltiorrhiza; Schisandra chinensis; oleanolic acid or a pharmaceutically acceptable salt thereof; Ganoderma lucidum; silymarin; α-lipoic acid, more preferably R isomer of α-lipoic acid; N-acetyl cysteine; Picrorhiza kurroa; and any combination thereof. In yet another preferred embodiment of the invention, an antioxidant component of the antioxidant formulation is selected from Salvia miltiorrhiza; Schisandra chinensis; oleanolic acid or a pharmaceutically acceptable salt thereof; Ganoderma lucidum; silymarin; α-lipoic acid, more preferably R isomer of α-lipoic acid; N-acetyl cysteine; Picrorhiza kurroa; oxymatrine; and any combination thereof.

In certain embodiments of the invention, a constituent may be used in the antioxidant formulation that is derived from any of the named antioxidant components or that are extracts of any of the named plant or herbal components. Such constituent may be used in replacement of or in addition to the antioxidant component from which it is derived and/or extracted. By means of non-limiting examples, any of the phenolic compounds isolated from an aqueous extract of Salvia miltiorrhiza; kutkin as an active principal of Picrorhiza kurroa; and apocynin, which may be isolated from Picrorhiza kurroa, may be included in the antioxidant formulation, either individually, or any combination thereof. PICROLIV® is a non-limiting example of a commercially available extract containing kutkin and, optionally, apocynin, available from Sabinsa Corporation (Piscataway, N.J.) that may be used in the antioxidant formulation. Of course, any other mixture and/or extract that contain one or more constituents derived from the antioxidant components of the antioxidant formulation may be used in replacement of or in addition to the antioxidant component or antioxidant components from which they are derived in the antioxidant formulation.

Any combination, as expressed herein, may include a combination of antioxidants or antioxidant components, HCV active constituents, and NASH active constituents, are intended to encompass any combination of two, three, etc. up to and including all of the components and/or constituents named herein for each respective combination of antioxidants or antioxidant components, HCV active constituents, and NASH active constituents. For example, formulations of the antioxidant, without limitation, may include Salvia miltiorrhiza, Schisandra chinensis, oleanolic acid, Ganoderma lucidum, silymarin, α-lipoic acid, N-acetyl cysteine, Picrorhiza kurroa, and any extract thereof; Salvia miltiorrhiza, N-acetyl cysteine, and any extract of the aforementioned plant or herbal components; Salvia miltiorrhiza, Schisandra chinensis, oleanolic acid, Ganoderma lucidum, N-acetyl cysteine, and any extract of the aforementioned plant or herbal components; oleanolic acid, Ganoderma lucidum or any extract thereof, silymarin, α-lipoic acid, and N-acetyl cysteine, oleanolic acid and silymarin; etc.

In one embodiment of the invention, the treatment regimen further comprises a supplemental formulation. Preferably, this supplemental formulation will comprise at least one component or constituent that retards the progression of fibrosis or even reverses an established fibrosis in the liver resulting from a particular condition. More preferably, the supplemental formulation will comprise at least one component or constituent that retards the progression of fibrosis or even reverses an established fibrosis in the liver resulting from a chronic HCV infection when provided in a therapeutically effective amount to a subject experiencing such a condition. In a preferred embodiment of the invention, the supplemental formulation for combating the effect on the liver due to a chronic HCV infection, otherwise referred to herein as an "HCV supplemental formulation," comprises one or more of *Picrorhiza kurroa*, an extract of *Picrorhiza kurroa*, baicalin/baicalein, and oxymatrine.

In another preferred embodiment of the invention, the supplemental formulation will comprise at least one component or constituent that retards the progression of fibrosis or even reverses an established fibrosis in the liver resulting from a non-alcoholic steatohepatitis when provided in a therapeutically effective amount to a subject experiencing such a condition. In a preferred embodiment of the invention, the supplemental formulation for combating the effect on the liver due to a non-alcoholic steatohepatitis, otherwise referred to herein as a "NASH supplemental formulation," comprises one or more of baicalin/baicalein, paeoniflorin, berberine, *Catalpa ovata* or extract thereof, and *Picrorhiza kurroa* or any extract thereof.

In yet another embodiment of the invention, a formulation, specifically, a formulation used in the treatment of chronic liver disease resulting from a chronic HCV infection, comprises at least one antioxidant and at least one component or constituent that retards the progression of fibrosis or even reverses an established fibrosis in the liver resulting from the chronic HCV infection when provided in a therapeutically effective amount to a subject experiencing such a condition. The antioxidant, in certain embodiments of the invention, comprises any of or even any combination of *Salvia miltiorrhiza; Schisandra chinensis*; oleanolic acid or a pharmaceutically acceptable salt thereof; *Ganoderma lucidum*; silymarin; α-lipoic acid, preferably R isomer of α-lipoic acid; N-acetyl cysteine, *Picrorhiza kurroa*, and any extract of the aforementioned plant or herbal components. In certain other embodiments of the invention, the antioxidant optionally comprises oxymatrine. In certain embodiments of the invention, the component or constituent that retards or even reverses fibrosis resulting from the chronic HCV infection is selected from the group consisting of *Picrorhiza kurroa*, an extract of *Picrorhiza kurroa*, baicalin/baicalein, oxymatrine, and any combination thereof. In a preferred embodiment of the invention, a formulation used in the treatment of chronic liver disease resulting from a chronic HCV infection, comprises *Salvia miltiorrhiza* or extract thereof; *Schisandra chinensis* or extract thereof; oleanolic acid or a pharmaceutically acceptable salt thereof; *Ganoderma lucidum* or extract thereof; silymarin; α-lipoic acid, more preferably R isomer of α-lipoic acid; N-acetyl cysteine; *Picrorhiza kurroa* or extract thereof; baicalin/baicalein; oxymatrine; and any combination thereof. Further to this preferred embodiment, any extract of the herbs of the formulation may be used in replacement of or in addition to the herb in the formulation.

In yet another embodiment of the invention, a formulation, specifically, a formulation used in the treatment of chronic liver disease resulting from a non-alcoholic steatohepatitis, comprises at least one antioxidant and at least one component or constituent for combating the effect on the liver due to the non-alcoholic steatohepatitis when provided in a therapeutically effective amount to a subject experiencing such a condition. The antioxidant, in certain embodiments of the invention, comprises any of or even any combination of *Salvia miltiorrhiza; Schisandra chinensis*; oleanolic acid or a pharmaceutically acceptable salt thereof; *Ganoderma lucidum*; silymarin; α-lipoic acid, preferably R isomer of α-lipoic acid; N-acetyl cysteine; *Picrorhiza kurroa*; any extract of the aforementioned plant or herbal components; and, optionally, oxymatrine. The antioxidant, in certain other embodiments of the invention, comprises any of or even any combination of *Salvia miltiorrhiza; Schisandra chinensis*; oleanolic acid or a pharmaceutically acceptable salt thereof; *Ganoderma lucidum*; silymarin; α-lipoic acid, preferably R isomer of α-lipoic acid; N-acetyl cysteine; *Picrorhiza kurroa*; any extract of the aforementioned plant or herbal components, and optionally, oxymatrine. In certain embodiments of the invention, the component or constituent that combats fibrosis resulting from the non-alcoholic steatohepatitis is selected from the group consisting of baicalin/baicalein, paeoniflorin, berberine, *Catalpa ovata, Picrorhiza kurroa*, any extract of the aforementioned plant or herbal constituents, and any combination thereof. In a preferred embodiment of the invention, a formulation used in the treatment of chronic liver disease resulting from a non-alcoholic steatohepatitis, comprises *Salvia miltiorrhiza* or extract thereof; *Schisandra chinensis* or extract thereof; oleanolic acid or a pharmaceutically acceptable salt thereof; *Ganoderma lucidum* or extract thereof; silymarin; α-lipoic acid, more preferably R isomer of α-lipoic acid; N-acetyl cysteine; *Catalpa ovata* or extract thereof; paeoniflorin; *Picrorhiza kurroa*; baicalin/baicalein; berberine; any extract thereof; and any combination thereof. Further to this preferred embodiment, any extract of the herbs of the formulation may be used in replacement of or in addition to the herb in the formulation.

Without intending to be bound by theory, embodiments of the invention provide improvements over other compositions or formulations known in the art by inhibiting fibrosis and possibly reversing cirrhosis caused by a fibrosis, which is responsible for many of the life-threatening complications associated with chronic hepatitis infection, non-alcoholic steatohepatitis, and chronic liver disease. Preferably, embodiments of the invention provide improvements over other compositions or formulations known in the art by inhibiting the progression of fibrosis or inducing fibrosis reversal in patients suffering from acute or chronic liver disease that is substantially free of side effects.

Without intending to be limiting, certain embodiments of the invention further provide improvements over compositions or formulations known in the art since the inventive compositions and formulations can be administered as part of a treatment therapy for acute or chronic liver disease, and the treatment therapy is affordable. Preferably, the inventive formulations are used in a therapy to treat chronic HCV infected patients, especially those patients who are non-responsive to conventional treatment therapies. In another preferred embodiment, the inventive formulations are used in a therapy to treat patients suffering from non-alcoholic steatohepatitis.

The inventors have conceived of a treatment regimen comprising one or more formulations that is an alternative medicine treatment for patients suffering from cirrhosis of the liver and specifically for patients with chronic liver disease. In certain embodiments of the invention, the alternative medicine treatment is used in a complimentary treatment strategy with other compositions and formulations to treat certain viral- or disease-induced fibrosis and cirrhosis of the liver. In preferred embodiments of the invention, the alternative medicine treatment is used as part of a treatment strategy for a patient who has contracted an HCV infection. In other preferred embodiments of the invention, the alternative medicine treatment is used as part of a treatment strategy for a patient who suffers from a steatohapatitis, more preferably NASH. In yet other embodiments of the invention, the alternative medicine treatment is used as part of a treatment strategy for a patient who suffers from alcoholic hepatitis. Indeed, the alternative medicine treatment may be used in a complimentary treatment strategy administered to a subject suffering any condition that has caused chronic liver disease.

As used herein, the acronym "ALT" refers to alanine amino transferase, a diagnostic liver function test. The test is also known as serum glutamate pyruvate transaminase (SGPT) or alanine aminotransferase (ALAT). Consistently elevated levels of ALT may suggest the existence of, among other medical problems, alcoholic or viral hepatitis. ALT is typically measured in units/liter (U/l).

As used herein, the acronym "AST" refers to aspartate aminotransferase, an enzyme that catalyzes the transfer of the amino group from glutamic acid to oxaloacetic acid forming alpha-ketoglutaric acid and aspartic acid. Elevated levels of AST can be a sign of acute liver damage. AST is typically expressed in units/liter (U/l).

As used herein, the term "bilirubin" is a compound that is excreted in bile. The level of bilirubin becomes elevated with certain diseases, in particular hepatitis or severe liver failure with cirrhosis.

As used interchangeably herein, the terms "cirrhosis" and "liver cirrhosis" refers to any stage in the development of the pathological condition, for example, from the initial development of scar tissue in the liver to advanced stages of fibrosis. Non-limiting examples of diseases or conditions that are known to lead to cirrhosis include alcoholism; Type B or Type C chronic viral hepatitis; chronic bile duct blockage; Wilson's disease or hemochromatosis, a metabolic diseases resulting in unusually high levels of copper iron, respectively, being stored in the body. Other causes of cirrhosis include, but are not limited to, exposure to drugs or other toxins; autoimmune processes such as autoimmune hepatitis; diseases that are inherited such as cystic fibrosis and alpha antitrypsin deficiency; and obesity, which is also known as fatty liver or nonalcoholic steatohepatitis. Yet, even other causes of cirrhosis can include severe reactions to drugs; prolonged exposure to environmental toxins; parasitic infection schistosomiasis; and repeated incidents of heart failure with liver congestion.

The term "extract," as used herein, means a substance or composition obtained from a plant or plant part. An extract may be composed of an exudate, i.e., a substance or composition found external to the plant or plant part; internal to the plant or plant part, but external to the cells of the plant or plant part; and/or within the cells of the plant or plant part. Chemical and/or physical action or actions, as understood in the art, are required to obtain an extract from a plant or plant part.

As used herein, the acronym "HAI" refers to Knodell histological activity index. HAI is a grading or scoring system for the assessment of liver damage and represents the summation of four individual scores reflecting periportal and/or bridging necrosis, intralobular degeneration and focal necrosis, portal inflammation, and fibrosis. HAI, as traditionally measured, ranges from 0-22. Modifications to the scoring system have been made in order to provide a more detailed assessment of, for example, fibrosis. A lower score represents little to no necrosis, inflammation, and/or fibrosis. Higher scores are intended to reflect that the liver has suffered more extensive damage.

As used herein, "HCV" refers to hepatitis C virus, which is a species of the hepacivirus genus of the Flaviviridae family of viruses.

The term "HCV active," as used herein, means therapeutically or pharmacologically active for purposes of treating a condition associated with an acute or chronic HCV infection. Preferably, an "HCV active" will be therapeutically or pharmacologically active for purposes of retarding a fibrosis and/or cirrhosis occurring in the liver of a subject or a fibrosis and/or cirrhosis that would otherwise occur in the liver of a subject resulting from an acute or chronic HCV infection. Preferably, an "HCV active" will also be therapeutically or pharmacologically active for purposes of reversing a fibrosis and/or cirrhosis occurring in the liver of a subject resulting from an acute or chronic HCV infection.

As used herein, "NASH" refers to non-alcoholic steatohepatitis, a condition that resembles alcoholic hepatitis, but, rather, is inflammation of the liver due to fat accumulation.

The term "NASH active," as used herein, means therapeutically or pharmacologically active for purposes of treating a condition associated with NASH. Preferably, a "NASH active" will be therapeutically or pharmacologically active for purposes of retarding a fibrosis and/or cirrhosis occurring in the liver of a subject or a fibrosis and/or cirrhosis that would otherwise occur in the liver of a subject resulting from NASH. Preferably, a "NASH active" will also be therapeutically or pharmacologically active for purposes of reversing a fibrosis and/or cirrhosis occurring in the liver of a subject resulting from NASH.

A "pharmaceutically acceptable carrier" as used herein refers to a non-toxic solid, semisolid or liquid filler, diluent, encapsulating material or formulation auxiliary of any conventional type. A "pharmaceutically acceptable carrier" is non-toxic to recipients at the dosages and concentrations employed, and is compatible with other ingredients of the formulation.

The term "pharmaceutically acceptable excipient" as used herein includes adjuvants, diluents, vehicles, or other auxiliary substances, such as those conventional in the art, which are readily available to the public. For example, pharmaceutically acceptable auxiliary substances include pH adjusting and buffering agents, tonicity adjusting agents, stabilizers, wetting agents and the like.

The term "pharmaceutically acceptable salt" as used herein is intended to mean a salt of a compound according to the invention that is, within the scope of sound medical judgment, suitable for use in contact with the tissue of a subject without at least one of undue toxicity, irritability, and allergic response, commensurate with a reasonable benefit to risk ratio and is effective for its intended use.

The terms "subject," "host," and "patient," as used herein, are used interchangeably to refer to an animal that is being treated with the present formulations, including, but not limited to, simians, humans, avians, felines, canines, equines, rodents, bovines, porcines, ovines, caprines, mammalian farm animals, mammalian sport animals, and mammalian pets. In preferred embodiments of the invention, the "subject," "host," or "patient" is a human.

The term "therapeutically effective amount" or "effective amount" as used herein, means that amount of an active agent, a compound, a drug, or a formulation, that elicits a desired biological or medicinal response in a tissue system of a subject, or in a subject, that is being sought by a researcher, veterinarian, medical doctor or other clinician. In preferred embodiments of the invention, the tissue system of a subject is a liver. The desired response can include interdicting, preventing, palliating, or alleviating an existing viral infection or disease in the subject that is being treated. In some embodiments, the desired response includes at least a reduction in one or more symptoms, disorders, or diseases of a hepaciviral infection in the subject under treatment.

One skilled in the art will recognize that the "therapeutically effective amount" of an active agent, a compound, a drug, or a formulation to be used in the instant invention can vary with factors, such as the particular subject, e.g., age, weight, diet, health, etc.; severity and complications of viral infection condition sought to be treated or prevented; severity and complications of the chronic liver disease sought to be treated or prevented; the mode of administration of the active agent, the compound, the drug, or the formulation; the particular active agent, compound, drug, or formulation used, etc. Standard procedures can be performed to evaluate the effect of the administration of an active agent, a compound, a drug, or a formulation to a subject, thus allowing a skilled artisan to determine the effective amount of the active agent, a compound, a drug, or a formulation to be administered to the subject. For example, the syndrome or symptoms of the viral infection or disease, such as, for example, fever or inflammation, etc., the count of virus, ALT, AST, bilirubin, and the like, can be measured from the subject prior to or after the administration of the active agent, the compound, the drug, or the formulation. In addition, techniques, such as surveys or animal models, can also be used to evaluate the effectiveness of an active agent, a compound, a drug, or a formulation in treating or preventing a chronic liver disease.

The term "therapeutically effective amount of time" as used herein means the amount of time needed to elicit a desired biological or medicinal response in a tissue system of a subject, or in a subject, that is being sought by a researcher, veterinarian, medical doctor or other clinician. The desired response includes interdicting, preventing, palliating, or alleviating an existing infection, disease, or the like in the subject that is being treated. In some embodiments of the invention, the desired response includes at least a reduction in one or more symptoms, disorders, or diseases of an infection, disease, or the like in the subject under treatment. In preferred embodiments of the invention, the desired response includes retarding a fibrosis or cirrhosis occurring in the liver. In another preferred embodiment, the desired response includes reversing a fibrosis or cirrhosis occurring in the liver. One skilled in the art will recognize that the "therapeutically effective amount of time" to be used in the instant invention can vary with factors, such as the particular subject, e.g., age, weight, diet, health, etc.; severity and complications of viral infection, chronic liver disease, and/or condition sought to be treated or prevented; the mode of administration of the active agent; the particular active agent used; and the like.

The terms "therapy," "treatment," "treating," and other like terms, as used interchangeably herein, refer to obtaining a desired pharmacologic and/or physiologic effect. The effect may be prophylactic in terms of completely or partially preventing a condition or disease or symptom thereof and/or may be therapeutic in terms of a partial or complete cure for a condition or disease and/or adverse affect attributable to the condition or disease. "Therapy" and/or "treatment," thus, for example, covers any therapy and/or treatment of a condition or disease in a mammal, preferably in a human, and includes at least one of: (a) preventing the condition or disease or symptom thereof from occurring in a subject which may be predisposed to the condition or disease but has not yet been diagnosed as having it; (b) inhibiting the condition or disease or symptom thereof, such as, arresting its development; and (c) relieving, alleviating or ameliorating the condition or disease or symptom thereof, such as, for example, causing regression of the condition or disease or symptom thereof.

The term "vehicle", as used herein refers to a non-toxic solid, semisolid or liquid filler, carrier, diluent, excipient, solubilizing agent, encapsulating material or formulation auxiliary of any conventional type, and encompasses all of the components of the composition other than the active pharmaceutical or active ingredient(s). Suitable vehicles include, but are not limited to, water, dextrose, glycerol, saline, ethanol, buffer, dimethyl sulfoxide, Cremaphor EL, and combinations thereof. The vehicle may contain additional agents such as wetting or emulsifying agents, or pH buffering agents. Other materials such as anti-oxidants, humectants, viscosity stabilizers, and similar agents may be added as necessary.

Because evidence suggests that oxidative stress can have a role in the mechanisms leading to liver injury, preferably, the formulations of the invention will comprise at least one antioxidant that is useful for treating oxidative stress. More preferably, the at least one antioxidant can treat the oxidative stress associated with chronic liver disease caused by, for example, chronic HCV infection or NASH. Even more preferably, the inventive formulation comprises more than one antioxidant whose combined therapeutic effect is greater than the therapeutic effect provided by the individual use of any one of the antioxidants.

Glutathione is an antioxidant, antitoxin, and enzyme cofactor that naturally occurs in cells. Glutathione is synthesized by the liver and becomes involved in DNA synthesis and repair, protein and prostaglandin synthesis, amino acid transport, metabolism of toxins and carcinogens, immune system function, preventing oxidative cell damage, and enzyme activation. Glutathione is a powerful antioxidant that also recycles other antioxidants such as vitamin C and vitamin E allowing them to remain in an active state. Studies have shown that a treatment regimen including glutathione inhibits tumor necrosis factor-alpha (TNF-$\alpha$) activity in subjects suffering from alcoholic hepatitis. See Hill et al., "Antioxidants Attenuate Nuclear Factor-Kappa B Activation and Tumor Necrosis Factor-Alpha Production in Alcoholic Hepatitis Patient Monocytes and Rat Kupffer Cells, in vitro," *Clin. Biochem.*, 32(7):563-70 (1999). Glutathione can be orally administered to a subject as L-glutathione, a pharmaceutically acceptable salt of glutathione.

N-acetyl cysteine is the N-acetyl derivative of the amino acid L-cysteine. N-acetyl cysteine is a precursor of glutathione but is, in many respects, a more efficient means of delivering glutathione to a subject. N-acetyl cysteine easily crosses a cell membrane, while glutathione cannot. Once N-acetyl cysteine has permeated the cell membrane, it is converted to cysteine and then to glutathione. Therefore, while reactive oxygen species such as hydrogen peroxide and hydroxyl-free radicals reduce intracellular and extracellular concentrations of glutathione, N-acetyl cysteine effectively replenishes glutathione and reduces any damage caused by these reactive oxygen species. N-acetyl cysteine, if taken alone, can have an irritating effect on the mucous membrane in the stomach and has an extremely bad taste. Further, N-acetyl cysteine becomes rapidly degraded and excreted from the body. A frequent dosage regimen is required in order to maintain a reasonable concentration of N-acetyl cysteine in the blood stream.

Ascorbic acid or ascorbate, a pharmaceutically acceptable salt of ascorbic acid, also better known as vitamin C, is a water-soluble vitamin that has been used in the treatment of chronic hepatitis. Ascorbic acid is derived from glucose via the uronic acid pathway; however, the enzyme L-gulonolactone oxidase, which converts gulonolactone to ascorbic acid is absent in primates requiring that the vitamin be a part of the human diet. Vitamin C has been reported to enhance glutathione regeneration in plasma and impart hepatotoxicity. See Hargreaves et al., "Studies on the Effects of L-Ascorbic Acid on Acetaminophen-Induced Hepatotoxicity II. An in vivo Assessment in Mice of the Protection Afforded by Various Dosage Forms of Ascorbate," *Toxicol. Appl. Pharmacol.*, 64(3):380-92 (1982).

*Ganoderma lucidum*, or Reishi mushrooms, are polypore mushrooms that are renowned for their medicinal properties. These mushrooms only flourish mainly on the dried trunks of dead plum, guercus serrata, or pasonia trees; therefore, they are scarce and remain largely undiscovered in the West. The Chinese name is Lingzhi, which means "spiritual potency," and has been recognized for over 2,000 years by Chinese medical professionals as a valuable remedy. A liquid fermentation broth of *Ganoderma lucidum* protected mice from hepatitis B virus activity. The study further showed that the cultured broth of *Ganoderm lucidum* supplemented with aqueous extract of Radix Sophorae flavescentis, a kind of Chinese herbal medicine, had better medicinal effects than simply mixing these two ingredients together. See Li et al., "Anti-Hepatitis Activities in the Broth of *Ganoderma lucidum* Supplemented with a Chinese Herbal Medicine," *Am. J. Chin. Med.*, 34(2):341-49 (2006).

Glycyrrhiza has been shown to be effective in treating patients suffering from a chronic HCV infection, in particular those patients who are not responsive to interferon therapy. See, e.g., Abe et al., "Effectiveness of Interferon, Glycyrrhizin Combination Therapy in Patients with Chronic Hepatitis C," *Nippon Rinsho.*, 52(7):1817-22 (1994). Glycyrrhizin can be extracted from the roots of licorice plants (*Glycyrrhiza glabra*). Licorice is important in traditional Chinese medicine (known as gancao, translated as "sweet grass" or "sweet herb"), and thus is extensively cultivated. While the exact mechanism is not clear, it has been proposed that glycyrrhizin has an inhibitory effect on immune mediated cytotoxicity against hepatocytes and on nuclear factor (NF)-kappa B, which activates genes encoding inflammatory cytokines in the liver.

Lipoic acid, also known as alpha-lipoic acid (α-lipoic acid), is a naturally occurring enzyme found in most prokaryotic and eukaryotic microorganisms as well as in plant and animal tissue. Lipoic acid's therapeutic potential has been recognized in conditions where oxidative stress is associated with liver damage. See Bustamante et al., "Alpha-Lipoic Acid in Liver Metabolism and Disease," *Free Radic. Biol. Med.*, 24(6):1023-39 (1998). Typically, only the R-enantiomer of lipoic acid occurs naturally. Indeed, more recent studies suggest that the S-enantiomer inhibits the effect of the R-enantiomer, substantially reducing its biological activity, increasing rather than reducing oxidative stress. Hence, embodiments of the invention that include α-lipoic acid will more preferably include R isomer α-lipoic acid or a racemic mixture wherein R isomer α-lipoic acid dominates over S isomer α-lipoic acid. See Loffelhardt et al., "Interaction of Alpha-Lipoic Acid Enantiomers and Homologues with the Enzyme Components of the Mammalian Pyruvate Dehydrogenase Complex," *Biochem. Pharmacol.*, 50(5): 637-46 (1995).

Oleanolic acid is a triterpenoid compound that exists widely in natural plants in the form of free acid or aglycones for triterpenoid saponins Oleanolic acid has been identified as a main bioactive constituent in many of the medicinal plans used in folk medicine. Oleanolic acid has been reported to demonstrate potent hepotoprotective activity. See, e.g., U.S. Pat. No. 6,884,908 to Srivastava et al.

*Salvia miltiorrhiza*, also known as Red sage, Chinese sage, tan shen, or dan shen, is a traditional Chinese medicinal herb used for the treatment of cardiovascular and hepatic diseases *Salvia miltiorrhiza* is a shade-growing perennial flowering plant in the genus *Salvia*. Seven phenolic compounds isolated from the aqueous extract of *Salvia miltiorrhiza* demonstrate a protective action against peroxidative damage to liver microsomes, hepatocytes, or erythrocytes. See Liu et al., "Protective Action of Seven Natural Phenolic Compounds Against Peroxidative Damage to Biomembranes", *Biochem. Pharmacol.*, 43(2):147-52 (1992).

*Schisandra* is derived from the berries that are harvested from *Schisandra chinensis*, a deciduous, dioecious woody vine that is a member of the Magnoliaceae family. Traditionally, *schisandra* has been distributed throughout northern and northeast China. The berries are harvested in the fall, dried, and ground for subsequent medicinal use. Studies have shown that *schisandra* protects the liver from lipid peroxidation or injury that is induced by carbon tetrachloride poisoning. See Liu, "Pharmacological Properties of Dibenzo [a, c] Cyclooctene Derivatives Isolated from Fructus *Shisandra Chinensis* III Inhibitory Effects on Carbon Tetrachloride-Induced Lipid Peroxidation, Metabolism and Covalent Binding and Carbon Tetrachloride to Lipids," *Chem. Biol. Interact.*, 41(1):39-47 (1982). *Schisandra* has been found to also be effective against viral and chemical induced hepatitis in subjects through certain mechanistic pathways, such as, lowering serum glutamic pyruvic transaminase (SGPT) levels, reducing ethanol induced malondialdehyde (MDA) formation, and increasing superoxide dismutase and catalase activities. Liu et al., "Effect of Dibenzo [a, c] Cyloocten Lignans Isolated from Fructus *Shisandra* on ADPH Induced Lipid Peroxidation (Malondialdehyde MDA) Formation) and Anti-Oxidative Enzyme Activity," *Chem. Biol. Interact.*, 78(1):77-84 (1991).

Silymarin is a mixture of three flavonolignans (silyban, silydianin, and silychristin) extracted from the seeds of the milk thistle plant *Silybum marianum*. Silymarin has been used as a Chinese and Ayurvedic medicine for well over 2,000 years. Additionally, Silymarin has notoriously been researched as a plant extract for the treatment of liver disease with over 450 publications addressing its use in such treatments. In particular, silybin or silibinin has been characterized as a hepato-protective substance. After ingesting silymarin and undergoing enterohepatic recirculation, high concentrations are found in liver cells. See Valnezuela et al., "Biochemical Bases of the Pharmacological Action of the Flavonoid Silymarin and of its Structural Isomer Silibinin," *Biol. Res.*, 27(2):105-12 (1994). Silymarin has also been shown to slow, or possibly reverse, liver fibrosis in animals. See Boigk et al., "Silymarin Retards Collagen Accumulation in Early and Advanced Biliary Fibrosis Secondary to Complete Bile Duct Obliteration in Rats," *Hepatology*, 26:643-49 (1997).

Vitamin B-complex represents eight water soluble vitamins, each playing an important role in cell metabolism. Vitamin B-complex includes thiamine (B1), riboflavin (B2), niacin (B3), pantothenic acid (B5), pyridoxine (B6), biotin (B7 or H), folic acid (B9), and cyanocobalamin (B12) each bearing similar properties that mostly work together synergistically. The therapeutic effects of B vitamins for treating chronic hepatitis have been investigated. In particular, vitamin B12 has proven to be useful in treating hepatitis by becoming stored in high concentrations in the liver and becoming available to participate in the regulation of hepatotropic virus functions. Specifically, vitamin B12 has been found to inhibit, however, not through a competitive binding mechanism, the HCV internal ribosome entry site (IRES)-dependent translation of a reporter gene in vitro in a dose-dependant manner without significantly affecting the cap-dependent mRNA resulting in a normalizing effect on the level of ALT in the bloodstream. Takyar et al., "Vitamin B12 Stalls the 80 S Ribosomal Complex on the Hepatitis C Internal Ribosome Entry Site," *J. Mol. Biol.*, 319(1):1-8 (2002).

Vitamin E is a fat-soluble vitamin that collectively includes eight naturally occurring compounds designated as either tocopherols or tocotrienols. α-Tocopherol, a powerful biological antioxidant, is the most active form of vitamin E in humans. It is believed that Vitamin E protects against liver damage induced oxidative stress by normalizing liver enzymes. See Sun et al., "Evaluation of Oxidative Stress Based on Lipid Hydroperoxide, Vitamin C and Vitamin E During Apoptosis and Necrosis Caused by Thioacetamide in Rat Liver," *Biochim. Biophys. Act.*, 1500(2):181-85 (2000). α-tocopherol, claimed to be the most important lipid-soluble antioxidant although the other vitamin E compounds have not been as thoroughly studied, also protects cell membranes from oxidation by reacting with lipid radicals produced in the lipid peroxidation chain reaction.

In a preferred embodiment of the invention, the antioxidant formulation comprises *Salvia miltiorrhiza*; *Schisandra chinensis*; oleanolic acid or a pharmaceutically acceptable salt thereof; *Ganoderma lucidum*; silymarin; α-lipoic acid, preferably the R isomer of α-lipoic acid; N-acetyl cysteine; *Picrorhiza kurroa*; and any combination thereof. In a more preferred embodiment of the invention, the antioxidant formulation comprises all of the aforementioned antioxidants. In another preferred embodiment of the invention, the antioxidant formulation comprises *Salvia miltiorrhiza*; *Schisandra chinensis*; oleanolic acid or a pharmaceutically acceptable salt thereof; *Ganoderma lucidum*; silymarin; α-lipoic acid, preferably the R isomer of α-lipoic acid; N-acetyl cysteine; *Picrorhiza kurroa*; any extract of the aforementioned plant or herbal components; and any combination thereof. Optionally, in certain preferred embodiments of the invention, the antioxidant formulation additionally comprises oxymatrine.

In certain embodiments of the invention, the antioxidant formulation comprises *Salvia miltiorrhiza* administered in a dose from about 0.1 mg/kg to about 100 mg/kg a day, from about 1 mg/kg to about 50 mg/kg a day, from about 2 mg/kg to about 20 mg/kg a day, and from about 10 mg/kg to about 15 mg/kg a day. In other embodiments of the invention, the antioxidant formulation comprising *Salvia miltiorrhiza* is administered twice a day ("bid") in which case the aforementioned dose of *Salvia miltiorrhiza* is reduced by one-half each time the antioxidant formulation is administered. In other embodiments of the invention, the antioxidant formulation comprising *Salvia miltiorrhiza* is administered three times a day ("tid") in which case the aforementioned dose of *Salvia miltiorrhiza* is reduced by one-third each time the antioxidant formulation is administered. In a preferred embodiment of the invention, the antioxidant formulation comprises *Salvia miltiorrhiza* administered in a dose from about 4.0 mg/kg to about 4.5 mg/kg tid.

In embodiments of the invention, the antioxidant formulation comprises *Salvia miltiorrhiza* in an amount in the range of about 1 mg to about 2,500 mg, from about 5 mg to about 1,500 mg, from about 25 mg to about 1,000 mg, and from about 50 mg to about 500 mg. In a preferred embodiment of the invention, the antioxidant formulation comprises *Salvia miltiorrhiza* in an amount in the range of about 250 mg to about 350 mg.

In certain embodiments of the invention, the antioxidant formulation comprises *Schisandra chinensis* administered in a dose from about 0.1 mg/kg to about 100 mg/kg a day, from about 1 mg/kg to about 50 mg/kg a day, from about 2 mg/kg to about 20 mg/kg a day, and from about 10 mg/kg to about 15 mg/kg a day. In other embodiments of the invention, the antioxidant formulation comprising *Schisandra chinensis* is administered bid in which case the aforementioned dose of *Schisandra chinensis* is reduced by one-half each time the antioxidant formulation is administered. In other embodiments of the invention, the antioxidant formulation comprising *Schisandra chinensis* is administered tid in which case the aforementioned dose of *Schisandra chinensis* is reduced by one-third each time the antioxidant formulation is administered. In a preferred embodiment of the invention, the antioxidant formulation comprises *Schisandra chinensis* administered in a dose from about 4.0 mg/kg to about 4.5 mg/kg tid.

In other embodiments of the invention, the antioxidant formulation comprises *Schisandra chinensis* in an amount in the range of about 1 mg to about 2,500 mg, from about 5 mg to about 1,500 mg, from about 25 mg to about 1,000 mg, and from about 50 mg to about 500 mg. In a preferred embodiment of the invention, the antioxidant formulation comprises *Schisandra chinensis* in an amount in the range of about 250 mg to about 350 mg.

In certain embodiments of the invention, the antioxidant formulation comprises oleanolic acid or a pharmaceutical acceptable salt thereof administered in a dose from about 0.05 mg/kg to about 75 mg/kg a day, from about 0.5 mg/kg to about 25 mg/kg a day, from about 1.5 mg/kg to about 10 mg/kg a day, and from about 7 mg/kg to about 10 mg/kg a day. In other embodiments of the invention, the antioxidant formulation comprising oleanolic acid or a pharmaceutical acceptable salt thereof is administered bid in which case the aforementioned dose of oleanolic acid or a pharmaceutical acceptable salt thereof is reduced by one-half each time the antioxidant formulation is administered. In other embodiments of the invention, the antioxidant formulation comprising oleanolic acid or a pharmaceutical acceptable salt thereof is administered tid in which case the aforementioned dose of oleanolic acid or a pharmaceutical acceptable salt thereof is reduced by one-third each time the antioxidant formulation is administered. In a preferred embodiment of the invention, the antioxidant formulation comprises oleanolic acid or a pharmaceutical acceptable salt thereof administered in a dose from about 2.5 mg/kg to about 3.0 mg/kg tid.

In other embodiments of the invention, the antioxidant formulation comprises oleanolic acid or a pharmaceutical acceptable salt thereof in an amount in the range of about 0.5 mg to about 2,000 mg, from about 2.5 mg to about 1,000 mg, from about 15 mg to about 750 mg, and from about 25 mg to about 300 mg. In a preferred embodiment of the invention, the antioxidant formulation comprises oleanolic acid or a pharmaceutical acceptable salt thereof in an amount in the range of about 150 mg to about 250 mg.

In certain embodiments of the invention, the antioxidant formulation comprises *Ganoderma lucidum* administered in a dose from about 0.1 mg/kg to about 200 mg/kg a day, from about 1 mg/kg to about 100 mg/kg a day, from about 3 mg/kg to about 50 mg/kg a day, and from about 20 mg/kg to about 25 mg/kg a day. In other embodiments of the invention, the antioxidant formulation comprising *Ganoderma lucidum* is administered bid in which case the aforementioned dose of *Ganoderma lucidum* is reduced by one-half each time the antioxidant formulation is administered. In other embodiments of the invention, the antioxidant formulation comprising *Ganoderma lucidum* is administered tid in which case the aforementioned dose of *Ganoderma lucidum* is reduced by one-third each time the antioxidant formulation is administered. In a preferred embodiment of the invention, the antioxidant formulation comprises *Ganoderma lucidum* administered in a dose from about 7.0 mg/kg to about 7.5 mg/kg tid.

In other embodiments of the invention, the antioxidant formulation comprises *Ganoderma lucidum* in an amount in the range of about 1 mg to about 5,000 mg, from about 5 mg to about 2,500 mg, from about 50 mg to about 1,050 mg, and from about 100 mg to about 750 mg. In a preferred embodiment of the invention, the antioxidant formulation comprises *Ganoderma lucidum* in an amount in the range of about 450 mg to about 550 mg.

In certain embodiments of the invention, the antioxidant formulation comprises silymarin administered in a dose from about 0.1 mg/kg to about 150 mg/kg a day, from about 1 mg/kg to about 75 mg/kg a day, from about 2.5 mg/kg to about 25 mg/kg a day, and from about 15 mg/kg to about 20 mg/kg a day. In other embodiments of the invention, the antioxidant formulation comprising silymarin is administered bid in which case the aforementioned dose of silymarin is reduced by one-half each time the antioxidant formulation is administered. In other embodiments of the invention, the antioxidant formulation comprising silymarin is administered tid in which case the aforementioned dose of silymarin is reduced by one-third each time the antioxidant formulation is administered. In a preferred embodiment of the invention, the antioxidant formulation comprises silymarin administered in a dose from about 5.5 mg/kg to about 6.0 mg/kg tid.

In other embodiments of the invention, the antioxidant formulation comprises silymarin in an amount in the range of about 1 mg to about 3,500 mg, from about 5 mg to about 2,000 mg, from about 25 mg to about 1,500 mg, and from about 50 mg to about 750 mg. In a preferred embodiment of the invention, the antioxidant formulation comprises silymarin in an amount in the range of about 350 mg to about 450 mg.

In certain embodiments of the invention, the antioxidant formulation comprises $\alpha$-lipoic acid, preferably R isomer $\alpha$-lipoic acid, administered in a dose from about 0.05 mg/kg to about 50 mg/kg a day, from about 0.5 mg/kg to about 25 mg/kg a day, from about 1 mg/kg to about 10 mg/kg a day, and from about 4.5 mg/kg to about 7.5 mg/kg a day. In other embodiments of the invention, the antioxidant formulation comprising $\alpha$-lipoic acid is administered bid in which case the aforementioned dose of $\alpha$-lipoic acid is reduced by one-half each time the antioxidant formulation is administered. In other embodiments of the invention, the antioxidant formulation comprising $\alpha$-lipoic acid is administered tid in which case the aforementioned dose of $\alpha$-lipoic acid is reduced by one-third each time the antioxidant formulation is administered. In a preferred embodiment of the invention, the antioxidant formulation comprises $\alpha$-lipoic acid, more preferably $\alpha$-lipoic acid, administered in a dose from about 2.5 mg/kg to about 3.0 mg/kg bid.

In other embodiments of the invention, the antioxidant formulation comprises $\alpha$-lipoic acid, preferably R isomer $\alpha$-lipoic acid, in an amount in the range of about 0.5 mg to about 2,000 mg, from about 2.5 mg to about 1,000 mg, from about 15 mg to about 750 mg, and from about 25 mg to about 300 mg. In a preferred embodiment of the invention, the antioxidant formulation comprises $\alpha$-lipoic acid, more preferably R isomer $\alpha$-lipoic acid, in an amount in the range of about 150 mg to about 250 mg.

In certain embodiments of the invention, the antioxidant formulation comprises N-acetyl cysteine administered in a dose from about 1 mg/kg to about 150 mg/kg a day, from about 1.5 mg/kg to about 75 mg/kg a day, from about 3 mg/kg to about 30 mg/kg a day, and from about 15 mg/kg to about 20 mg/kg a day. In other embodiments of the invention, the antioxidant formulation comprising N-acetyl cysteine is administered bid in which case the aforementioned dose of N-acetyl cysteine is reduced by one-half each time the antioxidant formulation is administered. In other embodiments of the invention, the antioxidant formulation comprising N-acetyl cysteine is administered tid in which case the aforementioned dose of N-acetyl cysteine is reduced by one-third each time the antioxidant formulation is administered. In a preferred embodiment of the invention, the antioxidant formulation comprises N-acetyl cysteine administered in a dose from about 8.2 mg/kg to about 8.8 mg/kg bid.

In other embodiments of the invention, the antioxidant formulation comprises N-acetyl cysteine in an amount in the range of about 1 mg to about 5,000 mg, from about 10 mg to about 3,000 mg, from about 50 mg to about 2,000 mg, and from about 100 mg to about 1,000 mg. In a preferred embodiment of the invention, the antioxidant formulation comprises N-acetyl cysteine in an amount in the range of about 550 mg to about 650 mg.

In certain embodiments of the invention, the antioxidant formulation comprises *Picrorhiza kurroa*, or extract thereof, administered in a dose from about 1 mg/kg to about 100 mg/kg a day, from about 2 mg/kg to about 50 mg/kg a day, from about 5 mg/kg to about 30 mg/kg a day, and from about 10 mg/kg to about 25 mg/kg a day. In other embodiments of the invention, the antioxidant formulation comprising *Picrorhiza kurroa*, or extract thereof, is administered bid in which case the aforementioned dose of *Picrorhiza kurroa*, or extract thereof, is reduced by one-half each time the antioxidant formulation is administered. In other embodiments of the invention, the antioxidant formulation comprising *Picrorhiza kurroa*, or extract thereof, is administered tid in which case the aforementioned dose of *Picrorhiza kurroa*, or extract thereof, is reduced by one-third each time the antioxidant formulation is administered. In a preferred embodiment of the invention, the antioxidant formulation comprises *Picrorhiza kurroa*, or extract thereof, administered in a dose from about 6 mg/kg to about 12.5 mg/kg bid.

In other embodiments of the invention, the antioxidant formulation comprises *Picrorhiza kurroa*, or extract thereof, in an amount in the range of about 1 mg to about 3,000 mg, from about 10 mg to about 2,500 mg, from about 50 mg to about 2,000 mg, and from about 100 mg to about 1,500 mg. In a preferred embodiment of the invention, the antioxidant formulation comprises *Picrorhiza kurroa*, or extract thereof, in an amount in the range of about 100 mg to about 1,000 mg.

In certain embodiments of the invention, at least one antioxidant formulation comprising at least one of *Salvia miltiorrhiza*; *Schisandra chinensis*; oleanolic acid or a pharmaceutically acceptable salt thereof; *Ganoderma lucidum*; silymarin; $\alpha$-lipoic acid, preferably the R isomer of $\alpha$-lipoic acid; N-acetyl cysteine; *Picrorhiza kurroa*; any extract of the aforementioned plant or herbal components; and any combination thereof is administered to a subject. Any of the antioxidant formulations may be administered at different time intervals and even by different means. For example, one of the at least one antioxidant formulations can be administered daily by oral administration and another of the at least one antioxidant formulations can be administered biweekly by infusion or injection.

Another aspect of the invention includes embodiments directed to supplementing a treatment using the antioxidant formulations of the invention using a supplemental formulation that is more specifically directed to the cause of fibrosis and/or cirrhosis occurring in the liver. Such therapies will be referred to herein as "combination" treatments and/or therapies. An embodiment of the invention comprises administering a supplemental formulation in a combination therapy that is directed to an HCV infection. Preferably, a supplemental formulation will be administered in a combination therapy in circumstances where the infection has either progressed to or is capable of becoming a chronic HCV infection.

In another embodiment of the invention, a supplemental formulation is administered in a combination therapy that is directed to the treatment of NASH. In yet other embodiments of the invention, a supplemental formulation is administered in a combination therapy that is directed to the treatment of alcohol induced cirrhosis or fibrosis. In even yet other embodiments of the invention, a supplemental formulation is administered in a combination therapy that is directed to the treatment of toxic chemical induced cirrhosis or fibrosis of the liver. Indeed, a supplemental formulation may be used in a combination therapy that is directed to any infection, disease, condition, or the like that leads to fibrosis and/or cirrhosis of the liver.

In certain embodiments of the invention, the supplemental formulation used in a combination therapy may be administered prior to, for a therapeutically effective amount of time, the administration of the antioxidant formulation. In certain embodiments of the formulation, the supplemental formulation used in a combination therapy may be administered substantially contemporaneously with the administration of the antioxidant formulation. In certain embodiments of the invention, the supplemental formulation used in a combination therapy may be administered following, for a therapeutically effective amount of time, the administration of the antioxidant formulation.

In certain embodiments of the invention, the supplemental formulation used in a combination therapy may be administered any of or even all of prior to, for a therapeutically effective amount of time; substantially contemporaneously with; and following, for a therapeutically effective amount of time, the administration of the antioxidant formulation. The therapeutically effective amount of time may be any time necessary to achieve a desired response, as further described herein.

In certain embodiments of the invention, the supplemental formulation will be administered in successive doses over the course of hours, days, weeks, etc. before the administration of the antioxidant formulation begins. Indeed, any number of treatments using the supplemental formulation may precede the antioxidant formulation over any required therapeutically effective amount of time.

Another aspect of the invention includes embodiments directed to a formulation using a combination that includes one or more constituents of the antioxidant formulations of the invention and one or more constituents more specifically directed to the cause of fibrosis and/or cirrhosis occurring in the liver. The formulation, according to an embodiment of the invention, comprises one or more constituents directed to an HCV infection. Preferably, the formulation will be administered in circumstances where the infection has either progressed to or is capable of becoming a chronic HCV infection.

The formulation, according to another embodiment of the invention, comprises one or more constituents directed to the treatment of NASH. In yet other embodiments of the invention, a formulation comprises one or more constituents directed to the treatment of alcohol induced cirrhosis or fibrosis. In even yet other embodiments of the invention, a formulation comprises one or more constituents directed to the treatment of toxic chemical induced cirrhosis or fibrosis of the liver. Indeed, a formulation may be used that comprises one or more constituents directed to any infection, disease, condition, or the like that leads to fibrosis and/or cirrhosis of the liver.

In certain embodiments of the invention, the formulation will be administered in successive doses over the course of hours, days, weeks, etc. In other embodiments of the invention, the formulation can be administered in a treatment regimen with any of the other formulations of the invention as described herein.

In other embodiments of the invention, the antioxidant formulation will be administered in successive doses over the course of hours, days, weeks, etc. before the administration of the supplemental formulation begins. Indeed, any number of treatments using the antioxidant formulation may precede the supplemental formulation over any required therapeutically effective amount of time.

In an embodiment of the invention, the therapy is a combination treatment involving the use of an antioxidant formulation of the invention and a supplemental formulation for treating fibrosis and/or cirrhosis caused by an HCV infection. The supplemental formulation for treating fibrosis and/or cirrhosis caused by an HCV infection includes at least one component or constituent that is therapeutically effective at treating fibrosis and/or cirrhosis caused by an HCV infection—i.e., an HCV active component or constituent. In certain embodiments of the invention, the supplemental formulation for treating fibrosis and/or cirrhosis caused by an HCV infection comprises at least one of *Picrorhiza kurroa*, any extract of *Picrorhiza kurroa*, baicalin/baicalein, and oxymatrine.

*Picrorhiza kurroa* is a small plant that grows at high altitudes in the western Himalayas. *Picrorhiza kurroa* is a well-known herb in the Ayurvedic system of medicine that has traditionally been used to treat, among other things, disorders of the liver. Picrorhiza, which is the dried rhizome of the herb *Picrorhiza kurroa*, demonstrates the ability to inhibit the generation of oxygen anions and to scavenge free radicals. Kutkin, comprised of kutkoside and the iridoid glycoside picrosides I, II, and III, is the active principal of *Picrorhiza kurroa*. However, apocynin, a cathecol, has been isolated from *Picrorhiza kurroa* and shown to be an effective anti-inflammatory agent because of its ability to prevent the formation of free radicals, oxygen ions, and peroxides in the body. Drosin and nine cucurbiacin glycosides have also been identified as active constituents of *Picrorhiza kurroa*.

While the hepatoprotective activity of *Picrorhiza kurroa* is not fully understood, it is believed to be attributed to the herb's ability to inhibit the generation of oxygen anions and to scavenge free radicals. Russo et al., "Indian Medicinal Plants as Antiradicals and DNA Cleavage Protectors," *Phytomedicine*, 8:125-β2 (2001). A randomized, double-blind, placebo-controlled trial including patients diagnosed with acute viral hepatitis were administered 375 mg of *Picrorhiza kurroa* root powder tid over a two week period. Bilirubin, serum glutamic-oxaloacetic transaminase, and serum glutamic pyruvic transaminase values were significantly lower in the treatment group when compared to the response of the placebo group. See Vaidya et al., "*Picrorhiza kurroa* (Kutaki) Royle ex Benth as a Hepatoprotective Agent—Experimental and Clinical Studies," *J. Postgrad. Med.*, 42:105-108 (1996).

Baicalin is a flavonoid that has been shown to affect γ-aminobutyric acid receptors, which is the chief inhibitory neurotransmitter in the mammalian central nervous system. Baicalin has also been characterized as having good anti-inflammatory activity. Baicalin can be isolated, for example, from extracts of *Scutellaria baicalensis*. In passing through the gastrointestinal tract, baicalin is converted to baicalein, a therapeutically active form of baicalin. In those formulations of the invention that are administered parenterally, transdermally, or any other forms of administration that avoid the digestive tract, a preferred formulation comprises baicalein. In formulations described herein, the term "baicalin/baicalein" will be interpreted to mean any of baicalin, baicalein, and combinations thereof.

Matrine and oxymatrine is found in several varieties of herbs including extracts of the sophora genus. Oxymatrine, the oxide of matrine, is converted to matrine, in the gastrointestinal tract. Matrine is believed to be more readily soluble than oxymatrine, and has been found to possess many medicinal properties possibly including use as a treatment for viral hepatitis.

In an embodiment of the invention, the HCV supplemental formulation comprises at least one HCV active. In certain embodiments of the invention, the HCV supplemental formulation comprises an HCV active selected from the group consisting of *Picrorhiza kurroa*, baicalin/baicalein, oxymatrine, and any combination thereof. In other embodiments of the invention, the HCV supplemental formulation comprises an HCV active selected from the group consisting of *Picrorhiza kurroa*, any extract of *Picrorhiza kurroa*, baicalin/baicalein, oxymatrine, and any combination thereof. In a preferred embodiment of the invention, the HCV supplemental formulation comprises an HCV active that includes at least one of *Picrorhiza kurroa* and any extract of *Picrorhiza kurroa*, baicalin/baicalein, and oxymatrine. In another preferred embodiment of the invention, the HCV supplemental formulation comprises an HCV active comprising only baicalin/baicalein.

In certain embodiments of the invention, the HCV supplemental formulation comprises *Picrorhiza kurroa*, and/or extract thereof, administered in a dose from about 0.02 mg/kg to about 25 mg/kg a day, from about 0.2 mg/kg to about 10 mg/kg a day, from about 0.4 mg/kg to about 5 mg/kg a day, and from about 1.5 mg/kg to about 3.5 mg/kg a day. In other embodiments of the invention, the HCV supplemental formulation comprising *Picrorhiza kurroa*, and/or extract thereof, is administered bid in which case the aforementioned dose of *Picrorhiza kurroa*, and/or extract thereof, is reduced by one-half each time the HCV supplemental formulation is administered. In other embodiments of the invention, the HCV supplemental formulation comprising *Picrorhiza kurroa*, and/or extract thereof, is administered tid in which case the aforementioned dose of *Picrorhiza kurroa*, and/or extract thereof, is reduced by one-third each time the HCV supplemental formulation is administered. In a preferred embodiment of the invention, the HCV supplemental formulation comprises *Picrorhiza kurroa*, and/or extract thereof, administered in a dose from about 1.1 mg/kg to about 1.8 mg/kg bid.

In other embodiments of the invention, the HCV supplemental formulation comprises *Picrorhiza kurroa*, and/or extract thereof, in an amount in the range of about 0.25 mg to about 1,500 mg, from about 2.5 mg to about 750 mg, from about 10 mg to about 500 mg, and from about 25 mg to about 250 mg. In a preferred embodiment of the invention, the HCV supplemental formulation comprises *Picrorhiza kurroa*, and/or extract thereof, in an amount in the range of about 50 mg to about 150 mg.

In certain embodiments of the invention, the HCV supplemental formulation comprises baicalin, baicalein, and any combination thereof, otherwise known herein as baicalin/baicalein, administered in a dose from about 0.04 mg/kg to about 50 mg/kg a day, from about 0.4 mg/kg to about 20 mg/kg a day, from about 0.8 mg/kg to about 10 mg/kg a day, and from about 2.5 mg/kg to about 7.5 mg/kg a day. In other embodiments of the invention, the HCV supplemental formulation comprising baicalin/baicalein is administered bid in which case the aforementioned dose of baicalin/baicalein is reduced by one-half each time the HCV supplemental formulation is administered. In other embodiments of the invention, the HCV supplemental formulation comprising baicalin/baicalein is administered tid in which case the aforementioned dose of baicalin/baicalein is reduced by one-third each time the HCV supplemental formulation is administered. In a preferred embodiment of the invention, the HCV supplemental formulation comprises baicalin/baicalein administered in a dose from about 2.5 mg/kg to about 3.0 mg/kg bid.

In other embodiments of the invention, the HCV supplemental formulation comprises baicalin/baicalein in an amount in the range of about 0.5 mg to about 2,000 mg, from about 2.5 mg to about 1,000 mg, from about 15 mg to about 750 mg, and from about 25 mg to about 300 mg. In a preferred embodiment of the invention, the HCV supplemental formulation comprises baicalin/baicalein in an amount in the range of about 150 mg to about 250 mg.

In certain embodiments of the invention, the HCV supplemental formulation comprises oxymatrine administered in a dose from about 0.06 mg/kg to about 75 mg/kg a day, from about 0.6 mg/kg to about 30 mg/kg a day, from about 1 mg/kg to about 20 mg/kg a day, and from about 5 mg/kg to about 10 mg/kg a day. In other embodiments of the invention, the HCV supplemental formulation comprising oxymatrine is administered bid in which case the aforementioned dose of oxymatrine is reduced by one-half each time the HCV supplemental formulation is administered. In other embodiments of the invention, the HCV supplemental formulation comprising oxymatrine is administered tid in which case the aforementioned dose of oxymatrine is reduced by one-third each time the HCV supplemental formulation is administered. In a preferred embodiment of the invention, the HCV supplemental formulation comprises oxymatrine administered in a dose from about 3 mg/kg to about 5 mg/kg bid.

In other embodiments of the invention, the HCV supplemental formulation comprises oxymatrine in an amount in the range of about 1 mg to about 2,500 mg, from about 5 mg to about 1,500 mg, from about 25 mg to about 1,000 mg, and from about 50 mg to about 500 mg. In a preferred embodiment of the invention, the HCV supplemental formulation comprises oxymatrine in an amount in the range of about 250 mg to about 350 mg.

In an embodiment of the invention, the therapy is a combination treatment involving the use of an antioxidant formulation of the invention and a supplemental formulation for treating fibrosis and/or cirrhosis caused by NASH. The supplemental formulation for treating fibrosis and/or cirrhosis caused by NASH includes at least one component or constituent that is therapeutically effective at treating fibrosis and/or cirrhosis caused by NASH—i.e., a NASH active component or constituent. In certain embodiments of the invention, the supplemental formulation for treating fibrosis and/or cirrhosis caused by NASH comprises at least one of *Catalpa ovata*, paeoniflorin, *Picrorhiza kurroa*, baicalin/baicalein, and berberine. In an embodiment of the invention, the supplemental formulation for treating fibrosis and/or cirrhosis caused by NASH comprises baicalin/baicalein, paeoniflorin, berberine *Catalpa ovata* and/or any extract thereof, *Picrorhiza kurroa* and/or any extract thereof, and any combination thereof.

The bark from the *Catalpa ovata*, or the Chinese *Catalpa*, tree was used in traditional Korean medicine as an anti-inflammatory agent. A methanol extract of this folk medicine has been shown to inhibit the productions of tumor necrosis factor-alpha (TNF-alpha) and nitric acid (NO) with significant decreases in mRNA levels of TNF-alpha and inducible NO synthase showing the bark may have therapeutic potential in controlling inflammatory disorders, for example, such as those associated with NASH. Pa et al., "Inhibitory Effects of the Stem Bark of *Catalpa ovata* G. Don. (Bignoniaceae) on the Productions of Tumor Necrosis Factor-α and Nitric Oxide by the Lipopolisaccharide-Stimulated RAW 264.7 Macrophages," *J. Ethnopharmacol.*, 88: 287-91 (2003). U.S. Pat. Publ. No. 2006/0160898 discloses that catalpic acid, present in the seeds of *catalpa* trees, has also been found to be medicinally useful in treating and even preventing Type 2 diabetes and associated disorders.

Paeoniflorin is one of the main effective components of the total glucosides of paeony (TGP) that is extracted from the root of *Paeonia lactiflora*. The anti-inflammatory, antioxidative, antihepatic injury and immunoregulatory activities of TGP are known in the art. The administration of paeoniflorin has been shown to significantly decrease the serum ALT activities in mice induced with an immunological liver injury. The increase in TNF-alpha, lipopolysaccharide binding protein, and CD14 mRNA (messenger ribonucleic acid) expression in mouse liver was significantly decreased by paeoniflorin and was changed by paeoniflorin at different timepoints after administering the compound. Liu et al., "Protective Effect of Paeoniflorin on Immunological Liver Injury Induced by Bacillus Calmette-Guerin plus Lipopolysaccharide: Modulation of Tumour Necrosis Factor-α and Interleukin-6 mRNA," *Clin. Exp. Pharmacol. Physiol.*, 33(4):332-39 (2006).

Berberine is a quaternary plant alkaloid from the group of isoquinoline alkaloids that is typically found in the roots, rhizomes, stems, and bark of such plants as *Berberis*, goldenseal (*Hydrastis canadensis*), and *Coptis chinensis*. Berberine has a long history of medicinal use in both Ayurvedic and Chinese medicine. It has been found that berberine hydrochloride attenuates hepatic fat degeneration of rats with fatty liver induced by a high-fat diet. Wang et al., "Effects of Berberine Hydrochloride on Nonalcoholic Fatty Liver Disease in Rats," *Journal of Lanzhou University (Medical Sciences)*, 33(4):8-11 (2007). The article stresses that decreased serum aminotransferase, triglyceride, low density lipid cholesterol, epididymal fat, and perirenal fat may be the result of improved insulin resistance.

In an embodiment of the invention, the NASH supplemental formulation comprises at least one NASH active. In certain embodiments of the invention, the NASH supplemental formulation comprises a NASH active selected from the group consisting of baicalin/baicalein, paeoniflorin, berberine, *Catalpa ovata*, *Picrorhiza kurroa*, any extract of the aforementioned plant or herbal actives, and any combination thereof. In a preferred embodiment of the invention, the NASH supplemental formulation comprises a NASH active that includes all of the aforementioned constituents. In another preferred embodiment of the invention, the NASH supplemental formulation comprises a NASH active comprising baicalin/baicalein, paeoniflorin, berberine, and *Catalpa ovata* or any extract thereof.

In certain embodiments of the invention, the NASH supplemental formulation comprises *Catalpa ovata*, and/or any extract thereof, administered in a dose from about 0.01 mg/kg to about 20 mg/kg a day, from about 0.1 mg/kg to about 10 mg/kg a day, from about 0.2 mg/kg to about 5 mg/kg a day, and from about 0.5 mg/kg to about 2.5 mg/kg a day. In other embodiments of the invention, the NASH supplemental formulation comprising *Catalpa ovata*, and/or any extract thereof, is administered bid in which case the aforementioned dose of *Catalpa ovata*, and/or any extract thereof, is reduced by one-half each time the NASH supplemental formulation is administered. In other embodiments of the invention, the NASH supplemental formulation comprising *Catalpa ovata*, and/or any extract thereof, is administered tid in which case the aforementioned dose of *Catalpa ovata*, and/or any extract thereof, is reduced by one-third each time the NASH supplemental formulation is administered. In a preferred embodiment of the invention, the NASH supplemental formulation comprises *Catalpa ovata*, and/or any extract thereof, administered in a dose from about 1.1 mg/kg to about 1.8 mg/kg a day.

In other embodiments of the invention, the NASH supplemental formulation comprises *Catalpa ovata*, and/or any extract thereof, in an amount in the range of about 0.25 mg to about 1,500 mg, from about 2.5 mg to about 750 mg, from about 10 mg to about 500 mg, and from about 25 mg to about 250 mg. In a preferred embodiment of the invention, the NASH supplemental formulation comprises *Catalpa ovata*, and/or any extract thereof, in an amount in the range of about 50 mg to about 150 mg.

In certain embodiments of the invention, the NASH supplemental formulation comprises paeoniflorin administered in a dose from about 0.01 mg/kg to about 20 mg/kg a day, from about 0.1 mg/kg to about 10 mg/kg a day, from about 0.2 mg/kg to about 5 mg/kg a day, and from about 0.5 mg/kg to about 2.5 mg/kg a day. In other embodiments of the invention, the NASH supplemental formulation comprising paeoniflorin is administered bid in which case the aforementioned dose of paeoniflorin is reduced by one-half each time the NASH supplemental formulation is administered. In other embodiments of the invention, the NASH supplemental formulation comprising paeoniflorin is administered tid in which case the aforementioned dose of paeoniflorin is reduced by one-third each time the NASH supplemental formulation is administered. In a preferred embodiment of the invention, the NASH supplemental formulation comprises paeoniflorin administered in a dose from about 1.1 mg/kg to about 1.8 mg/kg a day.

In other embodiments of the invention, the NASH supplemental formulation comprises paeoniflorin in an amount in the range of about 0.25 mg to about 1,500 mg, from about 2.5 mg to about 750 mg, from about 10 mg to about 500 mg, and from about 25 mg to about 250 mg. In a preferred embodiment of the invention, the NASH supplemental formulation comprises paeoniflorin in an amount in the range of about 50 mg to about 150 mg.

In certain embodiments of the invention, the NASH supplemental formulation comprises *Picrorhiza kurroa*, and/or any extract thereof, administered in a dose from about 0.01 mg/kg to about 20 mg/kg a day, from about 0.1 mg/kg to about 10 mg/kg a day, from about 0.2 mg/kg to about 5 mg/kg a day, and from about 0.5 mg/kg to about 2.5 mg/kg a day. In other embodiments of the invention, the NASH supplemental formulation comprising *Picrorhiza kurroa*, and/or any extract thereof, is administered bid in which case the aforementioned dose of *Picrorhiza kurroa*, and/or any extract thereof, is reduced by one-half each time the NASH supplemental formulation is administered. In other embodiments of the invention, the NASH supplemental formulation comprising *Picrorhiza kurroa*, and/or any extract thereof, is administered tid in which case the aforementioned dose of *Picrorhiza kurroa*, and/or any extract thereof, is reduced by one-third each time the NASH supplemental formulation is administered. In a preferred embodiment of the invention, the NASH supplemental formulation comprises *Picrorhiza kurroa*, and/or any extract thereof, administered in a dose from about 1.1 mg/kg to about 1.8 mg/kg a day.

In other embodiments of the invention, the NASH supplemental formulation comprises *Picrorhiza kurroa*, and/or any extract thereof, in an amount in the range of about 0.25 mg to about 1,500 mg, from about 2.5 mg to about 750 mg, from about 10 mg to about 500 mg, and from about 25 mg to about 250 mg. In a preferred embodiment of the invention, the NASH supplemental formulation comprises *Picrorhiza kur-*

*roa*, and/or any extract thereof, in an amount in the range of about 50 mg to about 150 mg.

In certain embodiments of the invention, the NASH supplemental formulation comprises baicalin, baicalein, and any combination thereof, otherwise known herein as baicalin/baicalein, administered in a dose from about 0.05 mg/kg to about 100 mg/kg a day, from about 0.5 mg/kg to about 50 mg/kg a day, from about 1 mg/kg to about 25 mg/kg a day, and from about 2 mg/kg to about 10 mg/kg a day. In other embodiments of the invention, the NASH supplemental formulation comprising baicalin/baicalein is administered bid in which case the aforementioned dose of baicalin/baicalein is reduced by one-half each time the NASH supplemental formulation is administered. In other embodiments of the invention, the NASH supplemental formulation comprising baicalin/baicalein is administered tid in which case the aforementioned dose of baicalin/baicalein is reduced by one-third each time the NASH supplemental formulation is administered. In a preferred embodiment of the invention, the NASH supplemental formulation comprises baicalin/baicalein administered in a dose from about 2.5 mg/kg to about 3 mg/kg bid.

In other embodiments of the invention, the NASH supplemental formulation comprises baicalin/baicalein in an amount in the range of about 0.5 mg to about 2,000 mg, from about 2.5 mg to about 1,000 mg, from about 15 mg to about 750 mg, and from about 25 mg to about 300 mg. In a preferred embodiment of the invention, the NASH supplemental formulation comprises baicalin/baicalein in an amount in the range of about 150 mg to about 250 mg.

In certain embodiments of the invention, the NASH supplemental formulation comprises berberine administered in a dose from about 0.1 mg/kg to about 200 mg/kg a day, from about 1 mg/kg to about 100 mg/kg a day, from about 2.5 mg/kg to about 50 mg/kg a day, and from about 10 mg/kg to about 25 mg/kg a day. In other embodiments of the invention, the NASH supplemental formulation comprising berberine is administered bid in which case the aforementioned dose of berberine is reduced by one-half each time the NASH supplemental formulation is administered. In other embodiments of the invention, the NASH supplemental formulation comprising berberine is administered tid in which case the aforementioned dose of berberine is reduced by one-third each time the NASH supplemental formulation is administered. In a preferred embodiment of the invention, the NASH supplemental formulation comprises berberine administered in a dose from about 5 mg/kg to about 6 mg/kg tid.

In other embodiments of the invention, the NASH supplemental formulation comprises berberine in an amount in the range of about 1 mg to about 3,500 mg, from about 5 mg to about 2,000 mg, from about 25 mg to about 1,500 mg, and from about 50 mg to about 750 mg. In a preferred embodiment of the invention, the NASH supplemental formulation comprises berberine in an amount in the range of about 350 mg to about 450 mg.

The formulations of the invention may be administered, for example, orally, parenterally, transdermally, epidurally, and intranasally.

Non-limiting examples of parenteral administration include subcutaneous, intramuscular, intraorbital, intracapsular, intraspinal, intrasternal, intravenous, intradermal, intraperitoneal, and intraportal. In preferred embodiments, the formulations of the invention are administered orally and are in the form of at least one of a powder, a solid, a capsule, a tablet, a gel, a solution, and an emulsion.

In an embodiment of the invention, the formulations of the invention are administered as a parenteral formulation. The constituents of the formulation may individually or as mixtures be combined with a pharmaceutically acceptable carrier or, optionally, a pharmaceutically acceptable excipient, when administered parenterally. For example, the constituents of the formulation may individually or as a mixture additionally comprise at least one of water, preferably sterile water and more preferably deionized, sterile water; normal saline; and any combination thereof when administered parenterally. Preferably when certain constituents of the formulation are available as solids, they will additionally comprise at least one of water, preferably sterile water and more preferably deionized, sterile water; normal saline; and any combination thereof. More preferably, such constituents will be delivered by infusion or intravenous injection.

In other embodiments of the invention, the constituents of the formulation may be administered using more than one type of the methods of administration. For example, some of the constituents of the formulation may be administered orally while other constituents are administered parenterally. In yet other embodiments, the formulations of the invention may have one or more or even all of the constituents split between more than one of the methods of administration. For example, at least one of the constituents may be partly delivered orally, the same constituent(s) may be partly delivered epidurally, and the remaining part of the same constituent(s) may be delivered parenterally. Indeed, any form or forms of delivery as could be conceived by a person having ordinary skill in the art with the benefit of this disclosure are intended to be encompassed within the invention.

In an embodiment of the invention, the formulations of the invention may be directly administered, optionally through a pharmaceutically acceptable carrier and/or a pharmaceutically acceptable excipient, such as through ingestion, by the subject. In certain embodiments of the invention, the formulations of the invention may be incorporated into food to be consumed by the subject. In yet other embodiments of the invention, the formulations of the invention may be included in dietary supplements to be taken by the subject. In even yet other embodiments of the invention, the formulations of the invention can be a part of a treatment regimen that are directly administered to a subject, optionally through a pharmaceutically acceptable carrier and/or a pharmaceutically acceptable excipient; incorporated into food to be consumed by the subject, included in dietary supplements to be taken by the subject; and any combination thereof.

A dietary supplement of the present invention may be provided in any variety of dosage forms using the formulations as disclosed herein. The preferred form of delivery of the dietary supplement of the present invention is through oral administration, although other forms may be used. Non-limiting examples of the oral forms of dietary supplements of the present invention include tablets; capsules, for example, vegetable capsules; hard gelatin capsules; and the like. For example, the formulations of the invention can be offered in the form of a tablet including a pharmaceutically acceptable carrier or a capsule including a pharmaceutically acceptable excipient. In an embodiment of the invention, the dietary supplement may be offered as a modified or extended release formulation.

In an embodiment, the formulations of the invention may be offered in more than one type of form for delivery. For example, more than one type of antioxidant formulation may be offered in two types of forms for delivery that are preferably administered at different times, depending on the therapeutic treatment that is attempting to be achieved. For example, two antioxidant formulations may be offered in the form of two dietary supplements with one being administered, for example, bid, and the other being administered, for example, tid. Preferably, when offered in more than one delivery form, each form will include indicium that clearly distinguishes to the user the different formulations. Instructions for use will advise the user, among other things, concerning how the dietary supplements are to be administered and the administration schedule. Examples of indicia include, but are not limited to, color coding, symbolic and/or textual markings, differing shapes of the dietary supplements, and the like. In other embodiments of the invention, multiple types of formulations may be offered in different bottles or can even be included in a blister pack. Preferably, when included in a blister pack, they formulations will be arranged such that it is clear to the user when the next formulation is to be administered and even whether a subject failed to timely administer an earlier formulation. Indeed, any form of packaging and form of delivery known in the art may be used in the invention.

With the benefit of this disclosure, a person having ordinary skill in the art can contemplate any number of forms of administration, administration schedules, and packaging. Such forms of administration, administration schedules and packaging are intended to be incorporated in this disclosure.

Other additives may be included in any of the formulations of the present invention to the extent that the therapeutic effects of the constituents of the formulation either acting individually or collectively on the subject are not affected or compromised. Indeed, such additives themselves may lead to a therapeutic benefit realized by the subject. Non-limiting examples of additives that may be included in the formulations of the invention include caffeine; water soluble vitamins, such as, for example, vitamin B1, vitamin B2, vitamin B6, vitamin B12, vitamin C, biotin, pantothenic acid, niacin also known as nicotinic acid, and any derivatives thereof; fat soluble vitamins, such as, for example, vitamin A, vitamin D, vitamin E, vitamin K, and any derivatives thereof; carnitine, more preferably L-carnitine; amino acids, such as, for example, taurine and arginine; any herb, such as, for example, ginseng, cinnamon, dandelion, chrysanthemum, ginkgo, licorice root, *Serenoa repens* or any extract thereof, *Hypericum perforatum* or any extract thereof, Echinacea, aniseed, annual chamomile also known as cammomile, rosemary, mint, eucalyptus, lavender, rose, hibiscus, aloe, and any extract thereof; calcium; and any other active compound, such as, for example, oligosaccharides, such as lactulose, or commercial lactic acid bacteria, such as bifidus. The type and amount of additives included in a formulation may be varied, as appropriate, depending on the characteristics of the subject in which the formulations of the invention are intended to be administered. Examples of such characteristics of the subject include, but are not limited to, age, sex, health, hereditary conditions, and the like. Indeed, some additives may be included in any of the formulations if the present invention to counteract a side effect that is common to one or more of the constituents of the formulation, either acting individually or collectively.

If necessary, formulations intended to be delivered orally may be coated with a sugar or a film that is soluble in the stomach or intestines, including, but not limited to, sucrose, gelatin, agar, pectin, hydroxypropyl cellulose, and hydroxypropyl methyl cellulose phthalate. In yet other embodiments of the invention, the formulations or any individual constituent or mixture of constituents thereof may be delivered as a time-release formulation such as a capsule, a microcapsule, a nanoparticle, and any combination thereof. Any time-release vehicle known in the art is intended to be incorporated into this disclosure. In one embodiment of the invention, 85% of the formulation of the invention is released from between about 1 hour to about 24 hours, from about 1 hour to about 12 hours, from about 1 hour to about 8 hours, and from about 2 hours to about 6 hours.

Another aspect of the invention includes methods of treating chronic liver disease. Preferably, the methods of treating chronic liver disease will comprise the step of administering at least one of the formulations of the invention.

In an embodiment of the invention, a method for treating a chronic liver disease comprises the step of administering at least one antioxidant formulation comprising *Salvia miltiorrhiza; Schisandra chinensis*; oleanolic acid or a pharmaceutically acceptable salt thereof; *Ganoderma lucidum*; silymarin; α-lipoic acid, preferably the R isomer of α-lipoic acid; N-acetyl cysteine; *Picrorhiza kurroa*, and any combination thereof. In certain embodiments of the invention, any extract of the herbs in the antioxidant formulation may be used in replacement of or in addition to the herbs from which they are extracted in the antioxidant formulation. In yet other embodiments of the invention, the antioxidant formulation may optionally comprise oxymatrine.

In certain embodiments of the invention, the method comprises the step of separately administering at least two antioxidant formulations each formulation comprising any of *Salvia miltiorrhiza; Schisandra chinensis*; oleanolic acid or a pharmaceutically acceptable salt thereof; *Ganoderma lucidum*, silymarin; α-lipoic acid, preferably R isomer of α-lipoic acid; N-acetyl cysteine; *Picrorhiza kurroa*; any extract of the plants or herbs thereof; and combinations thereof. For example, one of the at least two antioxidant formulations can be administered orally and another of the at least two antioxidant formulations can be administered by injection. In another embodiment of the invention, the at least two antioxidant formulations can be administered at different times and/or intervals. For example, one of the antioxidant formulations can be administered daily and the other of the antioxidant formulations can be administered biweekly. In certain embodiments of the invention, either or both of the at least two antioxidant formulations may optionally comprise oxymatrine.

In another embodiment of the invention, the method of treatment is for a chronic liver disease caused by a chronic HCV infection. In an embodiment of the invention the method of treating a chronic liver disease that is caused by a chronic HCV infection additionally comprises the step of administering at least one HCV supplemental formulation. In certain embodiments of the invention, the at least one HCV supplemental formulation comprises *Picrorhiza kurroa*, an extract of *Picrorhiza kurroa*, baicalin/baicalein, oxymatrine, and any combination thereof. In other embodiments of the invention, the HCV supplemental formulation comprises only baicalin/baicalein.

In an embodiment of the invention, a method for treating a chronic liver disease, wherein such disease is caused by a chronic HCV infection, comprises the steps of administering at least one antioxidant formulation comprising *Salvia miltiorrhiza, Schisandra chinensis*, oleanolic acid or a pharmaceutically acceptable salt thereof, *Ganoderma lucidum*, silymarin, α-lipoic acid, N-acetyl cysteine, *Picrorhiza kurroa*, any extract of the plants or herbs thereof, and any combination thereof and administering at least one HCV supplemental formulation comprising *Picrorhiza kurroa*, any extract of *Picrorhiza kurroa*, baicalin/baicalein, oxymatrine, and any combination thereof, wherein the at least one HCV supplemental formulation is administered at least one of prior to, for a therapeutically effective amount of time; substantially contemporaneously with; and following, for a therapeutically effective amount of time, administration of the at least one antioxidant formulation. In a preferred embodiment of the invention, the α-lipoic acid is the R isomer of α-lipoic acid. Optionally, in certain embodiments of the invention, the at least one antioxidant formulation comprises oxymatrine.

In another embodiment of the invention, the method of treatment is for a chronic liver disease caused by NASH. In an embodiment of the invention the method of treating a chronic liver disease that is caused by NASH additionally comprises the step of administering at least one NASH supplemental formulation. In certain embodiments of the invention, the at least one NASH supplemental formulation comprises baicalin/baicalein, paeoniflorin, berberine, *Catalpa ovata*, *Picrorhiza kurroa*, any extract of *Catalpa ovata*, any extract of *Picrorhiza kurroa*, and any combination thereof. In certain other embodiments of the invention, the at least one NASH supplemental formulation comprises baicalin/baicalein, paeoniflorin, berberine, and *Catalpa ovata* or any extract thereof.

In an embodiment of the invention, a method for treating a chronic liver disease, wherein such disease is caused by NASH, comprises the steps of administering at least one antioxidant formulation comprising *Salvia miltiorrhiza* and any extract thereof, *Schisandra chinensis* and any extract thereof, oleanolic acid or a pharmaceutically acceptable salt thereof, *Ganoderma lucidum* and any extract thereof, silymarin, α-lipoic acid, N-acetyl cysteine, *Picrorhiza kurroa* and any extract thereof, and any combination thereof and administering at least one NASH supplemental formulation comprising baicalin/baicalein, paeoniflorin, berberine, *Catalpa ovata* and any extract thereof, *Picrorhiza kurroa* and any extract thereof, and any combination thereof, wherein the at least one NASH supplemental formulation is administered at least one of prior to, for a therapeutically effective amount of time; substantially contemporaneously with; and following, for a therapeutically effective amount of time, administration of the at least one antioxidant formulation. In a preferred embodiment of the invention, the α-lipoic acid is the R isomer of α-lipoic acid. Optionally, in certain embodiments of the invention, the at least one antioxidant formulation comprises oxymatrine.

Another aspect of the invention provides a kit for treating chronic liver disease comprising at least one antioxidant formulation having an antioxidant selected from the group consisting of *Salvia miltiorrhiza*; *Schisandra chinensis*; oleanolic acid or a pharmaceutically acceptable salt thereof; *Ganoderma lucidum*; silymarin; α-lipoic acid, preferably R isomer of α-lipoic acid; N-acetyl cysteine; *Picrorhiza kurroa*, any extract of the plants or herbs thereof, and any combination thereof. Optionally, in certain embodiments of the invention, a kit for treating chronic liver disease comprises at least one antioxidant formulation, the at least one antioxidant formulation having oxymatrine.

In a preferred embodiment of the invention, the kit further comprises at least one supplemental formulation selected from the group consisting of an HCV supplemental formulation for treating a chronic liver disease caused by a chronic HCV infection and a NASH supplemental formulation for treating a chronic liver disease caused by NASH.

The formulations of the kit are in a form for delivery as described herein, including but not limited to intranasal administration, inhalation, oral administration, topical administration, intravenous administration, intraperitoneal administration and other parenteral administration. The kit may optionally include a delivery device, if needed, to facilitate such administration. The kit will also have instructions advising the user as to such administration. In embodiments where the kit includes more than one formulation, such as, for example, two or more antioxidant formulations, a supplemental formulation, and the like, the instructions will inform the user as to the coordinated use of the two or more formulations.

EXAMPLES

A rodent model of spontaneous liver fibrosis progression and of established advanced fibrosis was used to demonstrate whether antioxidant formulations supplemented with either HCV-specific or NASH-specific supplemental formulations in a combination therapy could be used to retard the progression of liver fibrosis or reverse an established fibrosis.

Example 1

The purpose of this experiment was to test for the potential of an antioxidant formulation, either alone or in combination with an HCV-specific or a NASH-specific supplemental formulation, to impede the progression of ongoing liver fibrosis in a model if Mdr2 knockout mice.

Abcb4 is a human gene that is associated with progressive familial intrahepatic cholestasis whereby bile is prevented from flowing from the liver. Mdr2 (Abcb4)−/− mice have been characterized as developing progressive liver fibrosis. Mdr2−/− knockout and Mdr2+/+ wildtype mice were bred. Age-matched groups of Mdr2−/− mice of both sexes were treated during spontaneous progression of liver fibrosis from 4 weeks of age to 10 weeks of age. Mdr2−/− female mice are known to develop more severe lesions than males; hence, the analyses for mice in each gender were reported separately.

Six healthy wildtype mice undergoing no intervention constituted the control group. Four-week old Mdr2−/− knockout mice with early onset of biliary fibrosis were used in the treatment portion of the study. Forty-seven mice received a daily application of an antioxidant cocktail comprising the formulation and dose identified in Table 1 ("Prep-X") in a 10 μl vehicle per g body weight by intragastic gavage. Mice receiving only the vehicle were used as the control group.

TABLE 1

| Component | Rodent Dose | | |
|---|---|---|---|
| | Prep-X mg/kg per day | Prep-X with HCV Add-On mg/kg per day | Prep-X with NASH Add-On mg/kg per day |
| | Each Formulation | | |
| *Salvia miltorhiza* | 48.0 | 48.0 | 48.0 |
| *Schisandra chinensis* | 48.0 | 48.0 | 48.0 |
| Oleanoate | 32.0 | 32.0 | 32.0 |
| *Ganoderma lucidum* | 80.0 | 80.0 | 80.0 |
| Silymarin | 64.0 | 64.0 | 64.0 |
| R isomer alpha lipoic acid | 21.5 | 21.5 | 21.5 |
| N-Acetyl Cysteine | 64.0 | 64.0 | 64.0 |
| | Components Added at Midpoint | | |
| *Picrorhiza kurroa* | — | 10.8 | 5.4 |
| Baicalin | — | 21.5 | 21.5 |
| Oxymatrine | — | 32.0 | — |
| *Catalpa ovata* | — | — | 5.4 |
| Paeoniflorin | — | — | 5.4 |
| Berberine | — | — | 64.0 |

Fifteen mice (nine males and six females) continued the daily treatment for six weeks. Sixteen mice (seven males and nine females) continued the treatment daily for three weeks. Beginning with the fourth week of the treatment regimen, these sixteen mice continued to receive Prep-X supplemented with an HCV-specific supplemental formulation whose formulation and dose is shown in Table 1. This treatment continued daily for three additional weeks. Sixteen other mice (six males and nine females) continued the daily treatment for three weeks. Beginning with the fourth week of the treatment regimen, these sixteen mice continued to receive Prep-X supplemented with a NASH-specific supplemental formulation whose constituents and dose are shown in Table 1. This treatment continued daily for three additional weeks. At 10 weeks, the age when untreated mice progress into advanced interstitial (biliary-type) fibrosis, the mice were sacrificed by cardiac puncture and exsanguination under general anesthesia. The livers and spleens of the mice were excised, weighed, and snap-frozen in liquid nitrogen for further analysis. All the mice were housed with 12-hour light-dark cycles and fed with water and standard rat/mouse pellet chow ad libitum. Table 2 shows the relative and total hepatic collagen content of the livers and the weights of the liver and spleen for each of the groups of mice.

hepatic collagen content for male mice, liver weights for male mice, and spleen weight for male mice.

FIG. 1A is an image, with five times magnification, of a representative liver section of a male mouse using connective tissue staining after undergoing treatment receiving only the vehicle over a six week period. FIG. 1B is an image, with five times magnification, of a representative liver section of a male mouse using connective tissue staining after undergoing treatment receiving Prep-X over a six week period with the HCV-specific supplemental formulation included at the midway point of the combination treatment. FIG. 1C is an image, with five times magnification, of a representative liver section of a male mouse using connective tissue staining after undergoing treatment receiving Prep-X over a six week period with the NASH-specific supplemental formulation included at the midway point of the treatment. These figures show no apparent difference in periportal (or portal tract) collagen. However, lobular (parenchymal) collagen is reduced with a loss of fibrotic septa and the liver architecture is improved in the

TABLE 2

| Experimental Group | | | Relative Collagen Content | Total Hepatic Collagen | Liver | Spleen |
|---|---|---|---|---|---|---|
| Intervention | Gender | Size | µg hydroxyproline/100 mg | µg hydroxyproline/liver | Weight g | Weight g |
| none; healthy controls | male | 6 | 12.7 ± 1.01 | 160 ± 6 | 1.27 ± 0.07 | 0.091 ± 0.001 |
| PREP-X vehicle only | male | 9 | 24.8 ± 1.44 | 593 ± 38 | 2.40 ± 0.11 | 0.146 ± 0.005 |
| Prep-X vehicle; HCV add-on at week 7 | male | 7 | 26.3 ± 1.54 | 618 ± 54 | 2.36 ± 0.08 | 0.147 ± 0.008 |
| Prep-X vehicle; NASH add-on at week 7 | male | 6 | 25.3 ± 0.80 | 436 ± 21 | 1.72 ± 0.05 | 0.098 ± 0.004 |
| PREP-X vehicle only | female | 6 | 24.7 ± 1.33 | 538 ± 60 | 2.20 ± 0.17 | 0.165 ± 0.011 |
| Prep-X vehicle; HCV add-on at week 7 | female | 9 | 26.0 ± 1.23 | 544 ± 36 | 2.09 ± 0.07 | 0.157 ± 0.010 |
| Prep-X vehicle; NASH add-on at week 7 | female | 10 | 27.8 ± 1.20 | 560 ± 35 | 2.01 ± 0.08 | 0.149 ± 0.005 |

The procedure for determining hydroxyproline includes taking two snap-frozen liver pieces representing between 10-20% of total liver mass from the right and median liver lobe—approximately 250-300 mg total. These portions are hydrolyzed in 2 ml 6N hydrochloric acid at 110° C. for 16 hours. Hydroxyproline content was determine in 5 µl of hydrolysate biochemically in a 96-well plate format assay. More detailed procedures for determining hydroxyproline content can be found in Schuppan et al., "Lancet Seminars: Liver Cirrhosis," Lancet, 371:838-51 (2008); Popov et al., "Mdr2 (Abcb4)−/− Mice Spontaneously Develop Sever Biliary Fibrosis vis Massive Dysregulation of Pro- and Antifibrogenic Genes," J. Hepatol, 43:1045-54 (2005); and Popov et al., "Halofuginone Induces Matrix Metalloproteinases in Rat Hepatic Stellate Cells via Activation of p38 and NFkappaB," J. Biol. Chem., 281:150980-98 (2006), all included herein by reference. Total hepatic hydroxyproline for each liver was determined by multiplying the weight of the liver by the relative hepatic hydroxyproline content determined above.

The statistical significance of the difference in data, expressed as means±standard error of mean, was evaluated using an unpaired, non-parametric Student's t-test with a probability of error, p-level, of 0.05 (hereinafter referred to as "t-test"). The t-test showed that the deviation of means between the following groups of samples were not statistically significant: relative collagen content for male mice, relative collagen content for female mice, total hepatic collagen content for female mice, liver weights for female mice, and spleen weight for female mice. On the other hand, the t-test showed that the deviation of means between the following groups of samples had statistical significance: total male mice receiving Prep-X over a six week period supplemented with the NASH-specific supplemental formulation at the midway point of the combination treatment, as shown in FIG. 1C.

Quantitative real-time reverse transcriptase-polymerase chain reaction (RT-PCR) results were obtained for each of the liver specimens. 150-200 mg liver tissues from two lobes were homogenized using a tissue homogenizer and total RNA was extracted using RNAPURE™ reagent (manufactured by PeqLab of Erlangen, Germany) according to the manufacturer's recommendations. Template cDNA was obtained by reverse transcription of 1 µg of total RNA and relative transcript levels were quantified by real-time RT-PCR on a LIGHTCYCLER® 1.5 (manufactured by Roche of Mannheim, Germany). Probes and primers for mouse procollagen α1(1), TFGβ1, TIMP-1, α-SMA, and β2-microglobulin designed to span exon-exon boundaries to exclude genomic DNA co-amplification were used in the study. Housekeeping gene β2-microglobulin was amplified in parallel reactions for normalization. More details concerning the use of this procedure and these probes can be found in Schuppan et al. and the two references to Popov et al. as further recited herein.

FIGS. 2A-2D respectively represent profibrogenic gene expression of procollagen α1(1) encoding the major scar collagen; tissue inhibitor of matrix metalloproteinase-1 ("TIMP-1"); profibrogenic, proliferating cholangiocyte-associated integrin alpha v beta 6; and interstitial collagenase matrix metalloproteinase-13 ("MMP-13"). The quantitative real-time RT-PCR results are expressed in arbitrary units relative to the internal standard β2-microglobulin mRNA. The data are expressed as x-fold increase (mean±standard error of mean) versus the livers from the wildtype control mice. The t-test showed that the deviation of means for gene expression between the following groups of samples had statistical significance: procollagen α1(1) encoding the major scar collagen for the male mice and the female mice, TIMP-1 for the female mice, cholangiocyte-associated integrin alpha v beta 6 for the female mice, and interstitial collagenase MMP-13 for the female mice. The t-test showed that the deviation of means for gene expression between the remaining groups of samples were not statistically significant.

Table 3 shows the total bilirubin content, ALT, and AST for each of the groups of mice.

TABLE 3

| Experimental Group | | | Bilirubin Content | ALT | AST |
|---|---|---|---|---|---|
| Intervention | Gender | Size | µmol/liter | units/liter | units/liter |
| none; healthy controls | male | 6 | 1.00 ± 0.11 | 91.67 ± 54.3 | 175.0 ± 39.0 |
| PREP-X vehicle only | male | 9 | 2.62 ± 1.24 | 363.4 ± 57.3 | 446.6 ± 55.5 |
| Prep-X vehicle; HCV add-on at week 7 | male | 7 | 2.64 ± 0.84 | 331.0 ± 54.6 | 447.0 ± 66.4 |
| Prep-X vehicle; NASH add-on at week 7 | male | 6 | 2.34 ± 0.67 | 355.5 ± 47.7 | 417.8 ± 62.7 |
| PREP-X vehicle only | female | 6 | 3.07 ± 1.0 | 572.0 ± 110.2 | 604.4 ± 52.7 |
| Prep-X vehicle; HCV add-on at week 7 | female | 9 | 2.60 ± 0.57 | 479.0 ± 94.9 | 488.3 ± 64.6 |
| Prep-X vehicle; NASH add-on at week 7 | female | 10 | 3.60 ± 1.2 | 386.4 ± 89.5 | 496.0 ± 59.7 |

The t-test showed that the deviation of means for these data points were not statically significant.

Summarizing of the results of Example 1, the Prep-X treatment supplemented with a NASH-specific formulation included at the midway point of combination treatment had a significant effect on fibrosis and fibrogenesis in Mdr2 knockout mice. No such effect was noticed in the Prep-X treatment supplemented with an HCV-specific formulation included at the midway point of the combination treatment. An antifibrotic effect, i.e., a significant decrease of liver collagen and an improvement in liver architecture, was shown in male Mdr2 knockout mice; however, total collagen in female Mdr2 knockout mice was not shown to decrease significantly with the use of the Prep-X/NASH formulation.

The central profibrogenic transcript (procollagen I mRNA) was significantly downregulated both in male and in female Mdr2 knockout mice. Also, the finding that profibrogenic transcripts for integrin alpha v beta 6 and TIMP-1 were significantly downregulated in female Mdr2 knockout mice supports the conclusion of an antifibrotic effect in these mice, despite no significant change was shown in total liver collagen. These beneficial changes were also reflected by a decrease, though not shown to be of statistical significance, of the liver transaminases, especially in female Mdr2 knockout mice having higher serum levels than their male counterparts.

Example 2

The purpose of this experiment was to test for the potential of an antioxidant formulation, either alone or in combination with an HCV-specific or a NASH-specific supplemental formulation, to reverse an established fibrosis stimulated by an injection regiment of thioacetamide (TAA).

Sixty-eight six-week-old male C57BL/6J mice were used in this study. Eight of these mice were used, without intervention under healthy controls, as the control group. Sixty mice were injected intraperitoneally three times a weak with escalation doses—0.1, 0.2, 0.3, 0.4 g/kg—of TAA for six weeks to induce liver fibrosis. Six of treated animals died during TAA-injunction and were excluded from the study. Three days following the last injection, eleven mice were sacrificed as a control for fibrosis induction. The remaining forty-three mice received a daily application of an antioxidant cocktail comprising the formulation and dose identified in Table 1 ("Prep-X") in a 10 µl vehicle per g body weight by intragastic gavage. Mice receiving only the vehicle were used as the control group. Fifteen mice continued the daily treatment for four weeks. Fourteen mice continued the treatment daily for two weeks. Beginning in the third week of the treatment regimen, these fourteen mice continued to receive Prep-X supplemented with an HCV-specific supplemental formulation whose constituents and dose are shown in Table 1. This treatment continued daily for two additional weeks. Fourteen other mice continued the daily treatment for three weeks. Beginning in the third week of the treatment regimen, these fourteen mice continued to receive Prep-X supplemented with a NASH-specific supplemental formulation whose constituents and dose are shown in Table 1. This treatment continued daily for two additional weeks. At 10 weeks, after undergoing four weeks of treatment, the mice were sacrificed by cardiac puncture and exsanguination under general anesthesia. The livers and spleens of the mice were excised, weighed, and snap-frozen in liquid nitrogen for further analysis. All the mice were housed with 12-hour light-dark cycles and fed with water and standard rat/mouse pellet chow ad libitum. Table 4 shows the relative and total hepatic collagen content of the livers and the weights of the liver and spleen for each of the groups of mice.

TABLE 4

| Experimental Group | | Relative Collagen Content | Total Hepatic Collagen | | |
|---|---|---|---|---|---|
| Intervention | Size | µg hydroxyproline/100 mg | µg hydroxyproline/liver | Liver Weight g | Spleen Weight g |
| none; healthy controls | 8 | 13.5 ± 0.95 | 177 ± 17.4 | 1.30 ± 0.044 | 0.076 ± 0.003 |

TABLE 4-continued

| Experimental Group | | Relative Collagen Content | Total Hepatic Collagen | | |
|---|---|---|---|---|---|
| Intervention | Size | μg hydroxyproline/100 mg | μg hydroxyproline/liver | Liver Weight g | Spleen Weight g |
| peak of fibrosis; fibrosis induction control | 11 | 25.3 ± 1.58 | 387 ± 33.3 | 1.51 ± 0.064 | 0.087 ± 0.004 |
| PREP-X vehicle only | 15 | 27.2 ± 0.95 | 369 ± 10.1 | 1.37 ± 0.055 | 0.081 ± 0.002 |
| Prep-X vehicle; HCV add-on at week 7 | 14 | 26.4 ± 0.53 | 383 ± 17.2 | 1.45 ± 0.062 | 0.090 ± 0.004 |
| Prep-X vehicle; NASH add-on at week 7 | 14 | 28.8 ± 1.09 | 369 ± 21.8 | 1.28 ± 0.044 | 0.087 ± 0.002 |

Relative hydroxyproline content and total hepatic collagen content was determined by the procedure earlier disclosed herein.

The differences between the means of the healthy control group without intervention and the control group for fibrosis induction had statistical significance with respect to the relative collagen content and the total collagen content but were not statistically significant for either liver weights or spleen weights using the t-test. The t-test showed that the deviation of means for the groups of mice undergoing different treatment methodologies was not statistically significant.

FIG. 3A is an image, with five times magnification, of a representative liver section of a healthy C57BL/6J mouse using connective tissue staining FIG. 3B is an image, with five times magnification, of a representative liver section of a mouse using connective tissue staining after TAA-induction for six weeks representing the control for fibrosis induction. FIG. 3C is an image, with five times magnification, of a representative liver section of a mouse using connective tissue staining after TAA-induction for six weeks and then undergoing treatment receiving only the vehicle over a four week period. FIG. 3D is an image, with five times magnification, of a representative liver section of a mouse using connective tissue staining after TAA-induction for six weeks and then undergoing treatment receiving Prep-X over a four week period with the HCV-specific supplemental formulation included at the midway point of the combination treatment. FIG. 3E is an image, with five times magnification, of a representative liver section of a mouse using connective tissue staining after TAA-induction for six weeks and then undergoing treatment receiving Prep-X over a four week period with the NASH-specific supplemental formulation included at the midway point of the combination treatment.

FIGS. 4A-4C respectively represent profibrogenic gene expression of procollagen α1(1) encoding the major scar collagen; TIMP-1; and interstitial collagenase MMP-13. The quantitative real-time RT-PCR results, determined by the procedure as further defined herein, are expressed in arbitrary units relative to the internal standard β2-microglobulin mRNA. The data are expressed as x-fold increase (mean±standard error of mean) versus the livers from the control mice. The t-test showed that the differences between the means of the healthy control group without intervention and the control group for fibrosis induction had statistical significance for each of the three gene expressions. The t-test showed that the deviation of means for the groups of mice undergoing different treatment methodologies for each of three gene expressions was not statistically significant.

Neither the HCV-specific nor the NASH-specific supplemental formulations used in a treatment regiment with Prep-X had a statistically significant affect on fibrosis and fibrogenesis in the model of reversal of established fibrosis induced by TAA. A significant decrease of liver collagen and an improvement in liver architecture when compared to untreated fibrotic mice is not demonstrated by this experiment. This was also supported by a lack of alterations in the expression of profibrogenic or fibrolytic genes in the animals that received Prep-X treatment.

All publications mentioned herein, including patents, patent applications, and journal articles are incorporated herein by reference in their entireties including the references cited therein, which are also incorporated herein by reference. The publications discussed herein are provided solely for their disclosure prior to the filing date of the present application. Nothing herein is to be construed as an admission that the present invention is not entitled to antedate such publication by virtue of prior invention. Neither should the citation of documents herein be construed as an admission that the cited documents are considered material to the patentability of the claims of the invention. Further, the dates of publication provided may be different from the actual publication dates which may need to be independently confirmed.

Many modifications and other embodiments of the invention set forth herein will come to mind to one skilled in the art to which this invention pertains having the benefit of the teachings presented in the descriptions herein and the associated drawings. For example, though various methods are disclosed herein, one skilled in the art will appreciate that various other methods now know or conceived in the art will be applied to a subject in conjunction with the methods of treatments or therapies disclosed herein. Therefore, it is to be understood that the inventions are not to be limited to the specific embodiments disclosed and that modifications and other embodiments are intended to be included within the scope of the appended claims.

That which is claimed:

1. A method for treating a chronic liver disease in a human or an animal in need thereof consisting essentially of the steps of:

administering an antioxidant formulation to the human or animal who also suffers from a hepatitis C virus infection or non-alcoholic steatohepatitis, the formulation consisting essentially of *Salvia miltiorrhiza* extract and *Picrorhiza kurroa* extract, wherein the formulation is about 1 mg to about 2,500 mg *Salvia miltiorrhiza* and about 1 mg to about 3,000 mg *Picrorhiza kurroa*.

2. The method of claim 1 wherein the antioxidant formulation is administered orally or by injection.

3. The method of claim 2, wherein the antioxidant formulation is administered daily or biweekly.

4. A method for treating a chronic liver disease in a human or an animal in need thereof consisting essentially of the steps of:

administering a first antioxidant formulation to the human or animal who also is suffering from a hepatitis C virus infection or non-alcoholic steatohepatitis, the first antioxidant formulation consisting essentially of *Salvia miltiorrhiza* extract and *Picrorhiza kurroa* extract, wherein the first antioxidant formulation is about 1 mg to about 2,500 mg *Salvia miltiorrhiza* and about 1 mg to about 3,000 mg *Picrorhiza kurroa* and a second antioxidant formulation consisting essentially of another component selected from the group consisting of baicalin/baicalein, *Ganoderma lucidum* extract, oleanolic acid, *Schisandra chinensis* extract, N-acetyl cysteine, alpha-lipoic acid, silymarin, paeoniflorin, and berberine, wherein the second antioxidant formulation is administered in therapeutically effective amounts intravenously, by tablet, by capsule, transdermally, epidurally, intranasally, or combinations thereof.

5. The method of claim 4, wherein the first and second antioxidant formulations are administered orally or by injection.

6. The method of claim 5, wherein the first and second antioxidant formulations are administered daily or biweekly.

7. The method of claim 1, wherein the first antioxidant formulation is administered prior to, for a therapeutically effective amount of time; substantially contemporaneously with; and following, for a therapeutically effective amount of time, administration of the second antioxidant formulation or vice versa.

8. A method for treating a chronic liver disease in a human or an animal in need thereof comprising the step of:

administering an antioxidant formulation to the human or an animal who also suffers from a hepatitis C virus infection or non-alcoholic steatohepatitis, the formulation comprising therapeutically effective amounts of *Salvia miltiorrhiza* extract, *Schisandra chinensis* extract, oleanolic acid, *Ganoderma lucidum* extract, silymarin, α-lipoic acid, N-acetyl cysteine, and *Picrorhiza kurroa* extract, wherein the formulation is administered intravenously, by tablet, by capsule, transdermally, epidurally, intranasally, or combinations thereof.

9. The method of claim 8, wherein the formulation further comprises a hepatitis C virus or non-alcoholic steatohepatitis supplemental formulation comprising an active constituent selected from the group consisting of baicalin/baicalein, berberine, paeoniflorin, and any combination thereof.

10. The method of claim 8, wherein the formulation is administered prior to, for a therapeutically effective amount of time; substantially contemporaneously with; and following, for a therapeutically effective amount of time, administration of a formulation comprising components selected from the group consisting of baicalin/baicalein, berberine, paeoniflorin, and any combination thereof.

* * * * *